US011423246B2

(12) United States Patent
Yokouchi

(10) Patent No.: US 11,423,246 B2
(45) Date of Patent: Aug. 23, 2022

(54) MEDICINE INSPECTION ASSISTANCE DEVICE, IMAGE PROCESSING DEVICE, IMAGE PROCESSING METHOD, AND PROGRAM

(71) Applicant: FUJIFILM Toyama Chemical Co., Ltd., Tokyo (JP)

(72) Inventor: Koji Yokouchi, Ashigarakami-gun (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/788,001

(22) Filed: Feb. 11, 2020

(65) Prior Publication Data
US 2020/0175319 A1 Jun. 4, 2020

Related U.S. Application Data

(63) Continuation of application No. PCT/JP2018/019856, filed on May 23, 2018.

(30) Foreign Application Priority Data

Aug. 25, 2017 (JP) .............................. JP2017-162544

(51) Int. Cl.
H04N 7/18 (2006.01)
G06K 9/62 (2022.01)
G06T 7/586 (2017.01)
G06T 7/13 (2017.01)
(Continued)

(52) U.S. Cl.
CPC ............ *G06K 9/6215* (2013.01); *G06T 5/002* (2013.01); *G06T 5/003* (2013.01); *G06T 5/50* (2013.01);
(Continued)

(58) Field of Classification Search
CPC ... A61J 3/00; A61J 7/02; A61J 7/0454; G01N 21/85; G01N 21/9508; G06K 2209/19;
(Continued)

(56) References Cited

U.S. PATENT DOCUMENTS 8,712,163 B1 4/2014 Osheroff
2013/0279774 A1 10/2013 Helgason et al.
(Continued)

FOREIGN PATENT DOCUMENTS

JP 5163985 B2 3/2013
JP 2013-66533 A 4/2013
(Continued)

OTHER PUBLICATIONS

International Preliminary Report on Patentability and English translation of the Written Opinion of the International Searching Authority (Forms PCT/IB/373 and PCT/ISA/237) for International Application No. PCT/JP2018/019856, dated Feb. 25, 2020.
(Continued)

*Primary Examiner* — Masum Billah
(74) *Attorney, Agent, or Firm* — Birch, Stewart, Kolasch & Birch, LLP

(57) ABSTRACT

A medicine inspection assistance device, an image processing device and an image processing method are provided that appropriately recognize identification information irrespective of whether the identification information is an engraved mark or a printed character. The image processing device that obtains a plurality of taken images of a medicine, performs a process of enhancing an engraved mark portion of the medicine based on at least one taken image among the taken images and generates a first enhanced image, performs a process of enhancing a printed character portion of the medicine based on at least one taken image among the taken images and generates a second enhanced image, collates an integrated image obtained by integrating the first enhanced image and the second enhanced image with each other, with a master image, and determines whether the medicine to be dispensed and the dispensed medicine are identical to each other or not.

20 Claims, 13 Drawing Sheets

(51) Int. Cl.
*G16H 30/40* (2018.01)
*G16H 20/13* (2018.01)
*G06T 5/00* (2006.01)
*G06T 5/50* (2006.01)
*H04N 5/235* (2006.01)
*G06V 10/141* (2022.01)
*G06V 10/145* (2022.01)

(52) U.S. Cl.
CPC ................ *G06T 7/13* (2017.01); *G06T 7/586* (2017.01); *G06V 10/141* (2022.01); *G06V 10/145* (2022.01); *G16H 20/13* (2018.01); *G16H 30/40* (2018.01); *H04N 5/2354* (2013.01); *G06T 2207/20192* (2013.01)

(58) Field of Classification Search
CPC ........... G06K 9/2036; G06K 2209/401; G06K 9/00201; G06T 5/001; G06T 7/0012; G06T 7/70; G16H 20/13
USPC ......................................................... 348/161
See application file for complete search history.

(56) References Cited

U.S. PATENT DOCUMENTS

| | | | |
|---|---|---|---|
| 2015/0355101 A1* | 12/2015 | Sun | G01N 21/8806 348/46 |
| 2016/0203291 A1 | 7/2016 | Ebata | |
| 2016/0210524 A1 | 7/2016 | Hasegawa | |
| 2017/0186152 A1 | 6/2017 | Sun | |
| 2017/0264867 A1 | 9/2017 | Amano et al. | |
| 2017/0305589 A1* | 10/2017 | Yuyama | B65B 57/00 |
| 2018/0177682 A1* | 6/2018 | Tanaka | A61J 7/0084 |

FOREIGN PATENT DOCUMENTS

| | | |
|---|---|---|
| JP | 2015-68765 A | 4/2015 |
| JP | 2015-232483 A | 12/2015 |
| JP | 2017-90194 A | 5/2017 |
| WO | WO 2015/046043 A1 | 4/2015 |
| WO | WO 2015/152225 A1 | 10/2015 |
| WO | WO 2016/047569 A1 | 3/2016 |
| WO | WO 2017/119276 A1 | 7/2017 |

OTHER PUBLICATIONS

International Search Report (Form PCT/ISA/210) for International Application No. PCT/JP2018/019856, dated Aug. 14, 2018, with an English translation.
Extended European Search Report, dated Aug. 6, 2020, for counterpart European Application No. 18849001.5.

* cited by examiner

MEDICINE INSPECTION ASSISTANCE DEVICE, IMAGE PROCESSING DEVICE, IMAGE PROCESSING METHOD, AND PROGRAM

CROSS-REFERENCE TO RELATED APPLICATIONS

The present application is a Continuation of PCT International Application No. PCT/JP2018/019856 filed on May 23, 2018 claiming priority under 35 U.S.C § 119(a) to Japanese Patent Application No. 2017-162544 filed on Aug. 25, 2017. Each of the above applications is hereby expressly incorporated by reference, in its entirety, into the present application.

BACKGROUND OF THE INVENTION

1. Field of the Invention

The present invention relates to a medicine inspection assistance device, an image processing device, an image processing method, and a program, and in particular, to a medicine inspection assistance device, an image processing device, an image processing method, and a program that identify a kind of a medicine from an image obtained by imaging the medicine.

2. Description of the Related Art

Medicines have information for identifying the medicines added thereon. By reading the identification information, the kind of a medicine can be identified. Methods of adding the identification information include medicines having engraved marks and medicines having printed characters.

Japan Patent Application Laid-Open No. 2015-232483 (hereinafter referred to as "PTL 1") describes a technique that uses photometric stereo to create a contour extraction image representing a height in grayscale (luminance) in an image, thereby inspects a scar and a printed character. According to the technique of PTL 1, it is possible to achieve image inspection that is hardly affected by an inclination of a workpiece or illumination and is robust against an environment.

CITATION LIST

PTL 1: Japan Patent Application Laid-Open No. 2015-232483

SUMMARY OF THE INVENTION

Characters or the like printed on a surface of a medicine have no convexoconcave on the surface. Accordingly, in a case where a contour extraction image is generated as in the device described in PTL 1, printed information cannot be recognized. In addition, it is left unknown whether the identification information has been added to a collation target medicine by mark engraving or added by character printing.

Accordingly, there is a problem in that it is unknown which image processing is preferable for a taken image.

The present invention has been made in view of such situations, and aims to provide a medicine inspection assistance device, an image processing device, an image processing method and a program that appropriately recognize identification information irrespective of whether the identification information is an engraved mark or a printed character.

To achieve the above object, an aspect of an image processing device includes: a master image obtaining unit configured to obtain a master image of a medicine to be dispensed based on prescription information; a taken image obtaining unit configured to obtain a plurality of taken images of a dispensed medicine, with emitting directions of light to a surface of the medicine different from each other; a first image processing unit configured to perform a process of enhancing an engraved mark portion of the medicine, based on at least one taken image among the taken images, and generate a first enhanced image; a second image processing unit configured to perform a process of enhancing a printed character portion of the medicine, based on the at least one taken image among the taken images, and generate a second enhanced image; an image integrating unit configured to integrate the first enhanced image and the second enhanced image with each other, and generate an integrated image; and a determining unit configured to collate the generated integrated image with the master image, and determine whether the medicine to be dispensed is identical to the dispensed medicine or not.

According to this aspect, the taken images of the dispensed medicine in which the light illumination directions to the surface are different from each other are obtained, the first enhanced image generated by performing the process of enhancing the engraved mark portion of the medicine is integrated with the second enhanced image generated by performing the process of enhancing the printed character portion of the medicine to generate the integrated image, and the integrated image is collated with the master image to determine whether the medicine to be dispensed is identical to the dispensed medicine or not. Accordingly, the identification information can be appropriately recognized irrespective of whether the identification information is an engraved mark or a printed character.

Preferably, the first image processing unit performs a process of increasing a luminance value at the engraved mark portion of the medicine, the second image processing unit performs a process of increasing a luminance value at the printed character portion of the medicine, and the image integrating unit compares the luminance value of the first enhanced image and the luminance value of the second enhanced image at corresponding positions with each other, and adopts the luminance value of a higher luminance. Accordingly, the integrated image can be appropriately generated.

Preferably, the first image processing unit performs a process of reducing a luminance value at the engraved mark portion of the medicine, the second image processing unit performs a process of reducing a luminance value at the printed character portion of the medicine, and the image integrating unit compares the luminance value of the first enhanced image and the luminance value of the second enhanced image at corresponding positions with each other, and adopts the luminance value of a lower luminance. In such a mode, the integrated image can be appropriately generated.

Preferably, a medicine detecting unit configured to detect an area where the medicine is imaged, from each of the taken images, is provided, and the first image processing unit and the second image processing unit perform the processes for the detected area. Accordingly, the areas to be processed can be limited, which can reduce the time required to the processes.

Preferably, the taken image obtaining unit obtains three or more taken images, and the first image processing unit generates the first enhanced image, based on the three or more taken images. Accordingly, the engraved mark portion of the medicine can be appropriately enhanced.

Preferably, the first image processing unit obtains three-dimensional information on the surface of the medicine by photometric stereo, and generates the first enhanced image. Accordingly, the engraved mark portion of the medicine can be appropriately enhanced.

Preferably, the second image processing unit performs at least one of a smoothing process, a sharpening process and an edge detecting process, and generates the second enhanced image. Accordingly, the printed character portion of the medicine can be appropriately enhanced.

Preferably, a similarity calculating unit configured to calculate a similarity indicating a degree at which the integrated image is similar to the master image, is provided, and the determining unit determines whether the medicine to be dispensed is identical to the dispensed medicine or not, based on the similarity. Accordingly, it can be appropriately determined whether the medicine to be dispensed is identical to the dispensed medicine or not.

Preferably, the similarity calculating unit calculates similarities between a plurality of the integrated images and a plurality of the master images, and the determining unit determines that the medicine to be dispensed is identical to the dispensed medicine, for a combination of the integrated image and the master image with a highest similarity. Accordingly, it can be appropriately determined whether the medicine to be dispensed is identical to the dispensed medicine or not.

To achieve the above object, an aspect of a medicine inspection assistance device includes: a prescription information obtaining unit configured to obtain prescription information; a master image obtaining unit configured to obtain a master image of a medicine to be dispensed, based on the prescription information; an illuminating unit configured to include a plurality of light sources that irradiate a surface of a dispensed medicine with light in a plurality of illumination directions different from each other; an imaging unit configured to image the medicine; an imaging control unit configured to control the illuminating unit and the imaging unit, and obtain a plurality of taken images of the medicine, with illumination directions of light to the medicine different from each other; a first image processing unit configured to perform a process of enhancing an engraved mark portion of the medicine, based on at least one taken image among the taken images, and generate a first enhanced image; a second image processing unit configured to perform a process of enhancing a printed character portion of the medicine, based on at the least one taken image among the taken images, and generate a second enhanced image; an image integrating unit configured to integrate the first enhanced image and the second enhanced image with each other, and generate an integrated image; and a determining unit configured to collate the generated integrated image with the master image, and determine whether the medicine to be dispensed is identical to the dispensed medicine or not.

According to this aspect, the taken images in which the light illumination directions to the surface of the dispensed medicine are different from each other are obtained, the first enhanced image generated by performing the process of enhancing the engraved mark portion of the medicine is integrated with the second enhanced image generated by performing the process of enhancing the printed character portion of the medicine to generate the integrated image, and the integrated image is collated with the master image to determine whether the medicine to be dispensed is identical to the dispensed medicine or not. Accordingly, the identification information can be appropriately recognized irrespective of whether the identification information is an engraved mark or a printed character.

Preferably, the imaging control unit obtains the taken images of the medicine irradiated with light by two or more light sources among the light sources of the illuminating unit. Accordingly, the printed character portion of the medicine can be appropriately enhanced.

Preferably, the illuminating unit irradiates a front side and a rear side of the medicine with light, and the imaging unit images the front side and the rear side of the medicine. Accordingly, an appropriate taken image can be obtained irrespective of the posture of the medicine.

Preferably, the illuminating unit includes a first light source configured to emit light in a first direction, a second light source configured to emit light in a second direction, a third light source configured to emit light in a third direction, and a fourth light source configured to emit light in a fourth direction, and the second direction is a direction opposite to the first direction in plan view of the surface, the third direction is a direction orthogonal to the first direction in plan view of the surface, and the fourth direction is a direction opposite to the third direction in plan view of the surface. Accordingly, a plurality of taken images of the medicine where light illumination directions to the medicine are different from each other, can be appropriately obtained.

To achieve the above object, an aspect of an image processing method includes: a master image obtaining step of obtaining a master image of a medicine to be dispensed, based on prescription information; a taken image obtaining step of obtaining a plurality of taken images of a dispensed medicine, with emitting directions of light to a surface of the medicine different from each other; a first image processing step of performing a process of enhancing an engraved mark portion of the medicine, based on at least one taken image among the taken images, and generating a first enhanced image; a second image processing step of performing a process of enhancing a printed character portion of the medicine, based on the at least one taken image among the taken images, and generating a second enhanced image; an image integrating step of integrating the first enhanced image and the second enhanced image with each other, and generating an integrated image; and a determining step of collating the generated integrated image with the master image, and determining whether the medicine to be dispensed is identical to the dispensed medicine or not.

According to this aspect, the taken images in which the light illumination directions to the surface of the dispensed medicine are different from each other are obtained, the first enhanced image generated by performing the process of enhancing the engraved mark portion of the medicine is integrated with the second enhanced image generated by performing the process of enhancing the printed character portion of the medicine to generate the integrated image, and the integrated image is collated with the master image to determine whether the medicine to be dispensed is identical to the dispensed medicine or not. Accordingly, the identification information can be appropriately recognized irrespective of whether the identification information is an engraved mark or a printed character.

To achieve the above object, an aspect of a program is a program causing a computer to execute: a master image obtaining function of obtaining a master image of a medicine to be dispensed, based on prescription information; a taken image obtaining function of obtaining a plurality of taken images of a dispensed medicine, with emitting directions of light to a surface of the medicine different from each other; a first image processing function of performing a process of enhancing an engraved mark portion of the medicine, based on at least one taken image among the taken images, and generating a first enhanced image; a second image processing function of performing a process of enhancing a printed character portion of the medicine, based on the at least one taken image among the taken images, and generating a second enhanced image; an image integrating function of integrating the first enhanced image and the second enhanced image with each other, and generating an integrated image; and a determining function of collating the generated integrated image with the master image, and determining whether the medicine to be dispensed is identical to the dispensed medicine or not.

According to this aspect, the taken images in which the light illumination directions to the surface of the dispensed medicine are different from each other are obtained, the first enhanced image generated by performing the process of enhancing the engraved mark portion of the medicine is integrated with the second enhanced image generated by performing the process of enhancing the printed character portion of the medicine to generate the integrated image, and the integrated image is collated with the master image to determine whether the medicine to be dispensed is identical to the dispensed medicine or not. Accordingly, the identification information can be appropriately recognized irrespective of whether the identification information is an engraved mark or a printed character.

According to the present invention, irrespective of whether the identification information is an engraved mark or a printed character, the identification information can be appropriately recognized.

DESCRIPTION OF THE PREFERRED EMBODIMENTS

Hereinafter, with reference to the accompanying drawings, preferred embodiments of the present invention are described in detail.

First Embodiment

A medicine inspection assistance device according to a first embodiment is a device that audits a medicine by collating a master image with a taken image. The medicine inspection assistance device accurately performs collation irrespective of whether identification information added to the medicine has been added by mark engraving or by character printing.

Note that addition by mark engraving means that the identification information is formed by forming a groove that is a depressed (recessed) area on a surface of a medicine. The groove is not limited to what has been formed by scraping the surface. Alternatively, the groove may be what has been formed by pressing the surface. The engraved mark may include what does not have an identification function, such as of a cleavage line.

Addition by character printing means that the identification information is formed by adding edible ink or the like through contact or noncontact on a surface of a tablet. Here, addition by character printing has the same meaning as that of addition by printing.

Figure 1:
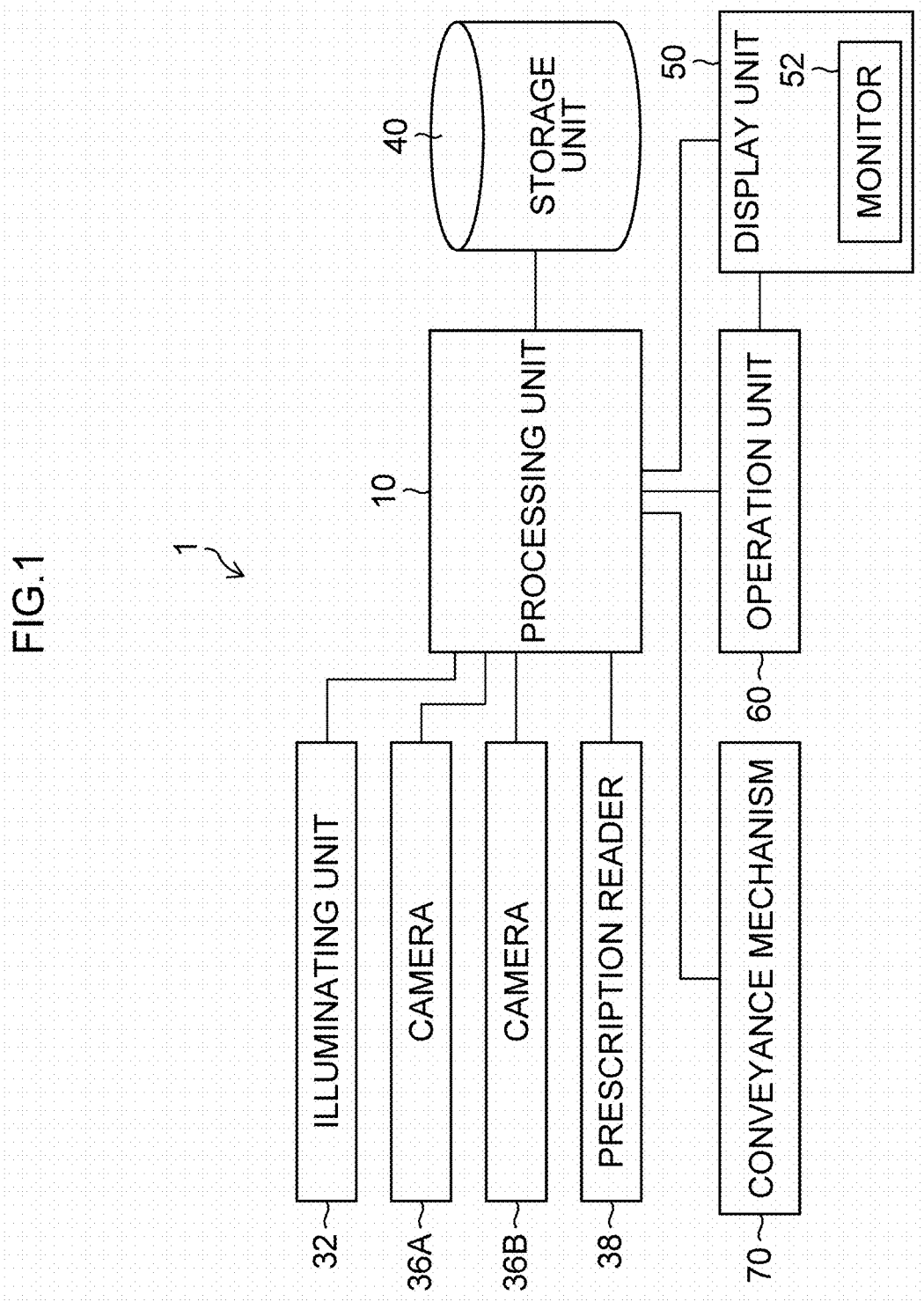
FIG. 1 shows a configuration of a medicine inspection assistance device.

FIG. 1 shows a configuration of a medicine inspection assistance device 1 according to the first embodiment. The medicine inspection assistance device 1 includes a processing unit 10, a storage unit 40, a display unit 50, an operation unit 60 and a conveyance mechanism 70. Furthermore, an illuminating unit 32, a camera 36A, a camera 36B and a prescription reader 38 are connected to the processing unit 10.

Figure 2:
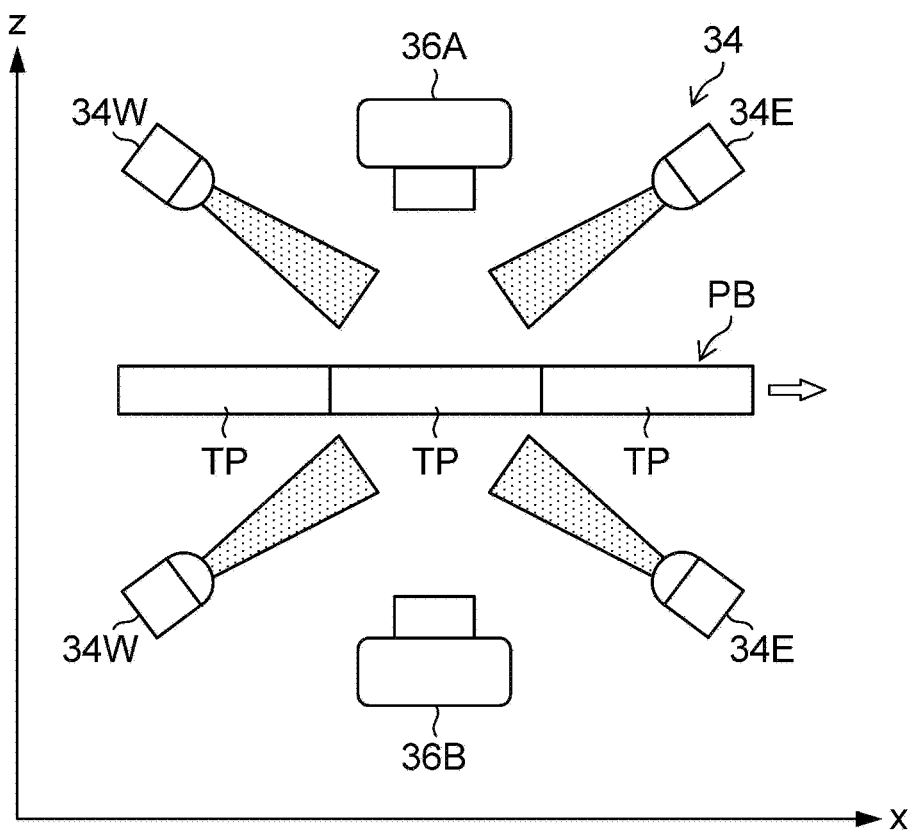
FIG. 2 is a side view showing situations where images of a divided package are obtained.
Figure 3:
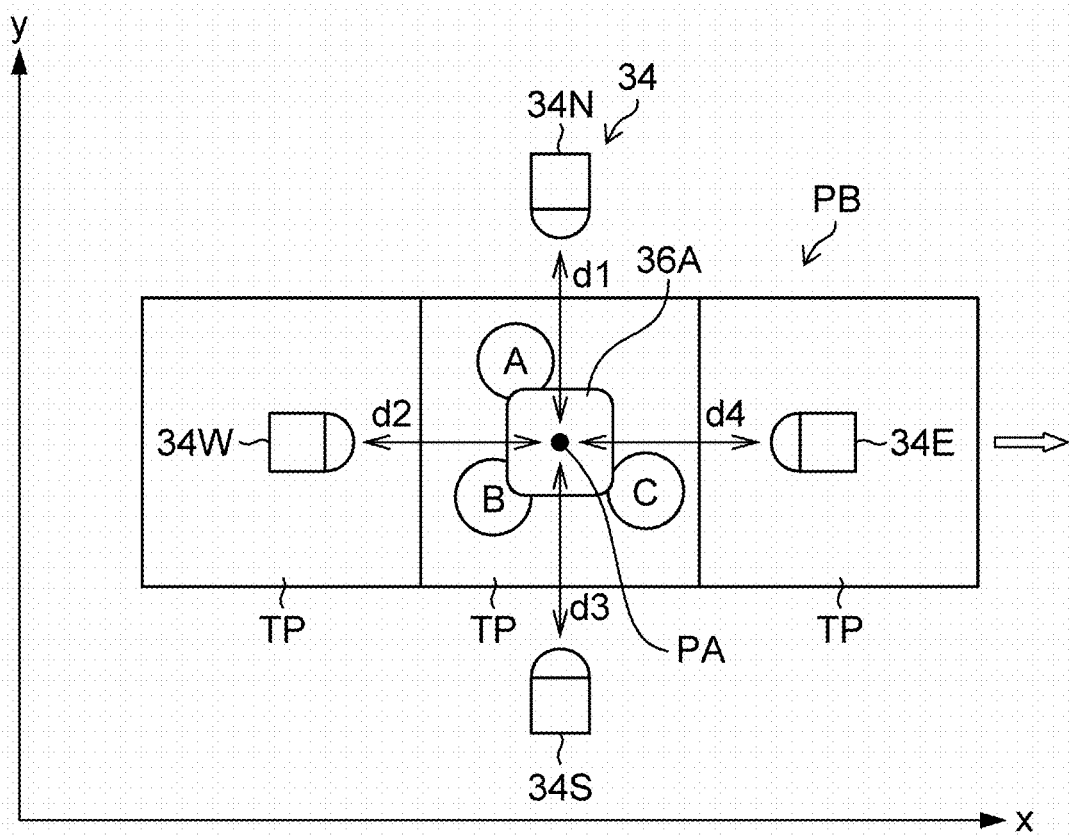
FIG. 3 is a top view showing situations of where images of a divided packages are obtained.

FIG. 2 is a side view showing situations of obtaining images of a divided package. FIG. 3 is a top view thereof.

The illuminating unit 32 includes a plurality of light sources 34 that each irradiate, with light, a strip medicine package PB including divided packages TP in series. In each of the divided packages TP, a dispensed medicine is packaged in a divided manner. As the light sources 34, four light sources 34N, 34S, 34E and 34W are arranged on each of an upper side (+z direction side in FIG. 2) and a lower side (−z direction side in FIG. 2) of the strip medicine package PB. Note that illustration of the light sources 34N and 34S on the upper side and the lower side of the strip medicine package PB is omitted in FIG. 2, and illustration of the four light sources 34N, 34S, 34E and 34W on the lower side of the strip medicine package PB is omitted in FIG. 3.

The light sources 34N (example of first light source), 34S (example of second light source), 34E (example of third light source) and 34W (example of fourth light source) on the upper side of the strip medicine package PB emit light respectively in −y direction (example of first direction), +y direction (example of second direction), −x direction (example of third direction) and +x direction (example of fourth direction) in the xy-plan view of FIG. 3. That is, the illumination direction of the light source 34S is the direction opposite to the illumination direction of the light source 34N in xy-plan view, the illumination direction of the light source 34E is the direction orthogonal to the illumination direction of the light source 34N in xy-plan view, and the illumination direction of the light source 34W is the direction opposite to the illumination direction of the light source 34E in xy-plan view.

The light sources 34N, 34S, 34E and 34W on the lower side of the strip medicine package PB are also arranged in a similar manner. Accordingly, the illuminating unit 32 irradiates the front side and the rear side of (the medicine packaged in) the divided package TP with light.

Each of the cameras 36A and 36B (example of imaging unit) includes a digital camera. As shown in FIG. 2, the camera 36A is arranged on the upper side of the strip medicine package PB, and the camera 36B is arranged on the lower side of the strip medicine package PB. The cameras 36A and 36B image the front side and the rear side of (the medicine packaged in) the divided package TP.

The divided packages TP (strip medicine package PB) are conveyed by the conveyance mechanism 70 in +x direction (the longitudinal direction of the strip medicine package PB) in FIG. 3. During imaging, the upper side of the divided package TP is illuminated in four directions by the light sources 34N, 34S, 34E and 34W above the divided package TP, and the lower side of the divided package TP is illuminated in four directions by the light sources 34N, 34S, 34E and 34W below the divided package TP. Note that it is preferable that the divided package TP be not irradiated with light other than the light emitted from the light sources 34 during imaging.

As shown in FIG. 3, the distances (d1, d2, d3 and d4) between the respective light sources 34N, 34S, 34E and 34W above the divided package TP and the imaging optical axis PA of the camera 36A are the same as each other. That is, the light sources 34 are apart from the imaging optical axis PA by the same distance (d1=d2=d3=d4). The light sources 34N, 34S, 34E and 34W below the divided package TP and the camera 36B are also arranged in a similar manner.

The medicine inspection assistance device 1 may be provided with a stage on which the divided packages TP are placed. In this case, the stage may be made of a material that transmits the light emitted from the light sources 34N, 34S, 34E and 34W below the divided package TP.

The prescription reader 38 shown in FIG. 1 (example of prescription information obtaining unit) reads a prescription and obtains prescription information. For example, information on a patient's name, prescribed medicines and their quantities and the like are read from a prescription written on a paper through OCR (Optical Character Recognition). If a bar code or the like indicating information pertaining to the prescribed medicines is recorded on the prescription, information on the prescribed medicines and their quantities and the like may be read from the bar code. Alternatively, a user may read a prescription, and input prescription information through an input device, such as a keyboard included in the operation unit 60. The prescription information obtained by the prescription reader 38 is stored in the storage unit 40.

The storage unit 40 may include a non-transitory recording medium, such as a CD (Compact Disk), a DVD (Digital Versatile Disk), a hard disk, and various semiconductor memories. In addition to the prescription information and the master images, the taken images obtained by the cameras 36A and 36B or processed taken images (images based on taken images) which have been subjected to image processing are stored in the storage unit 40 in association with each other.

The display unit 50 includes a monitor 52, and can display the prescription information obtained from the prescription reader 38, the taken images of the medicines packaged in divided packages, the master images stored in the storage unit 40 and the like. The operation unit 60 includes a pointing device such as a mouse, and an input device such as a keyboard. The user can operate images, buttons and the like displayed on the monitor 52 through the operation unit 60.

The conveyance mechanism 70 conveys the divided packages TP (strip medicine package PB) in the +x direction in FIG. 3.

[Configuration of Processing Unit]

Figure 4:
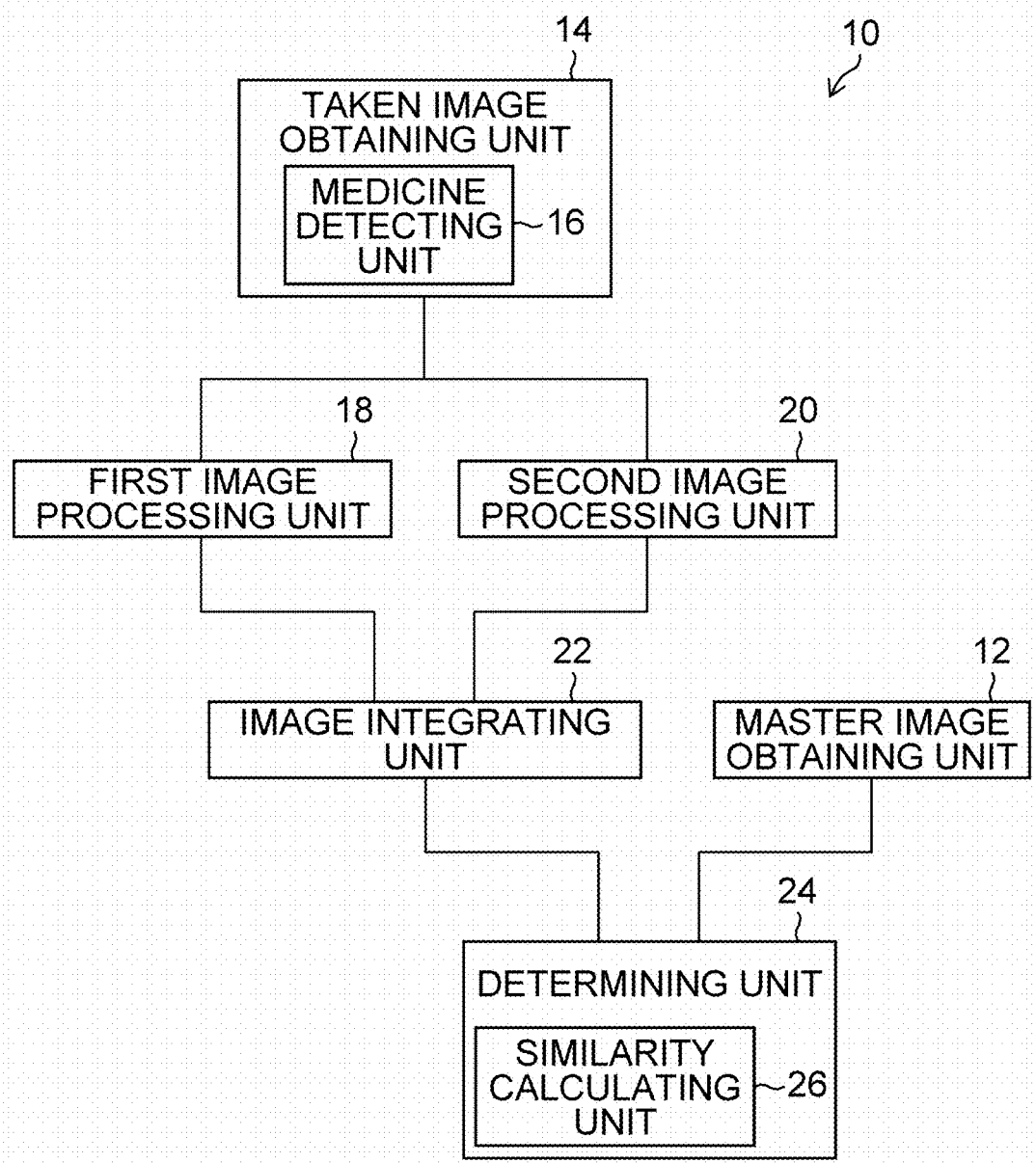
FIG. 4 shows an internal configuration of a processing unit.

FIG. 4 shows the internal configuration of the processing unit 10 (example of image processing device). As shown in FIG. 4, the processing unit 10 includes a master image obtaining unit 12, a taken image obtaining unit 14, a first image processing unit 18, a second image processing unit 20, an image integrating unit 22 and a determining unit 24.

The master image obtaining unit 12 reads and obtains master images of the prescribed medicines from the storage unit 40 based on the prescription information obtained from the prescription reader 38. Each master image is a reference image of a medicine, or a processed image obtained by applying image processing to the reference image. The master image is represented such that a luminance value of the identification information is relatively high in comparison with values of the other portions. The master images include a pair of master images that are a master image on one side and a master image on the other side for one medicine, and are preliminarily stored in the storage unit 40 in association with each other.

The taken image obtaining unit 14 (example of imaging control unit) controls the illuminating unit 32 and the cameras 36A and 36B, and obtains a plurality of taken images where the light illumination directions to the surface of each medicine packaged in the divided package TP are different from each other. The taken image obtaining unit 14 further includes a medicine detecting unit 16. The medicine detecting unit 16 detects an area (areas) where the medicine is taken, from each of the obtained taken images.

The first image processing unit 18 performs a process of enhancing an engraved mark portion of a medicine based on at least one taken image among the taken images obtained by the taken image obtaining unit 14, and generates a first enhanced image. In a case where the first enhanced image is generated based on a plurality of taken images, the process of enhancing the engraved mark portion of the medicine is applied to each of the taken images, and then the processed images are composed by addition or multiplication.

The second image processing unit 20 performs a process of enhancing a printed character portion of a medicine based on at least one taken image among the taken images obtained by the taken image obtaining unit 14, and generates a second enhanced image. In a case where the second enhanced image is generated based on a plurality of taken images, the process of enhancing the printed character portion of the medicine is applied to each of the taken images, and then the processed images are composed by addition or multiplication.

The image integrating unit 22 integrates the first enhanced image generated by the first image processing unit 18 and the second enhanced image generated by the second image processing unit 20, and generates an integrated image as a collation target image (image to be collated).

The determining unit 24 collates integrated images generated by the image integrating unit 22 with the master images obtained by the master image obtaining unit 12, and determines whether the medicine (medicines) to be dispensed according to the prescription is the same as the medicine (medicines) packaged in the divided package TP or not.

The determining unit 24 includes a similarity calculating unit 26. The similarity calculating unit 26 calculates the similarity indicating a degree at which the integrated images generated by the image integrating unit 22 are similar to the master images obtained by the master image obtaining unit 12. The determining unit 24 collates the integrated images with the master images based on the similarity.

The detailed processes of the medicine inspection assistance method according to these functions are described later.

[Processes of Medicine Inspection Assistance Method]

Figure 5:
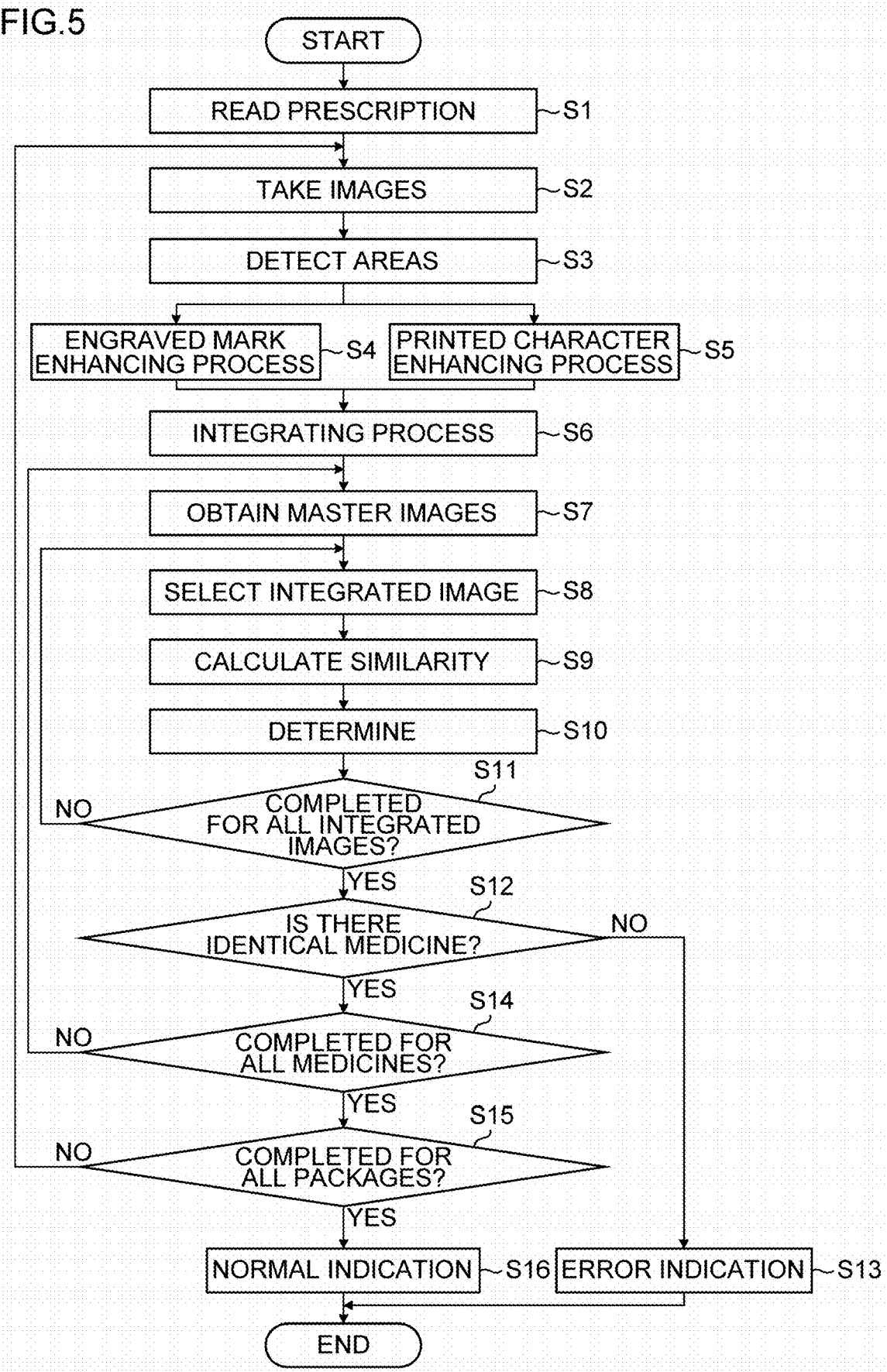
FIG. 5 is a flowchart showing processes of a medicine inspection assistance method.

A medicine inspection assistance method (example of image processing method) by the medicine inspection assistance device 1 is described. FIG. 5 is a flowchart showing the processes of the medicine inspection assistance method.

In step S1, a prescription is read by the prescription reader 38 to obtain the prescription information. Prescription information preliminarily stored in the storage unit 40 may be used.

In step S2 (example of taken image obtaining step, and example of taken image obtaining function), the taken image obtaining unit 14 controls the illuminating unit 32 and the cameras 36A and 36B to image medicines packaged in a divided package TP of the strip medicine package PB and obtain a plurality of taken images.

Here, the taken image obtaining unit 14 sequentially turns on the light sources 34N, 34S, 34E and 34W above the divided package TP one by one and turns off the others to sequentially switch the illumination direction in which the divided package TP is irradiated, and causes the camera 36A to image the divided package TP repeatedly every time the illumination direction is switched. Accordingly, the taken image obtaining unit 14 obtains taken images of the upper side of the divided package TP, which are taken with four illumination directions different from each other.

The taken image obtaining unit 14 sequentially turns on the light sources 34N, 34S, 34E and 34W below the divided package TP one by one and turns off the others to thus sequentially switch the illumination direction in which the divided package TP is irradiated, and causes the camera 36B to image the divided package TP repeatedly every time the illumination direction is switched. Accordingly, the taken image obtaining unit 14 obtains taken images of the lower side of the divided package TP, which are taken with four illumination directions different from each other.

Furthermore, it may be possible to image the divided package TP by the camera 36A in a state where all the light sources 34N, 34S, 34E and 34W (example of two or more light sources) above the divided package TP are turned on, to obtain a taken image (full-lighting image). Alternatively, it may be possible to image the divided package TP by the camera 36B in a state where all the light sources 34N, 34S, 34E and 34W below the divided package TP are turned on, to obtain a taken image.

In step S3, the medicine detecting unit 16 detects areas (medicine areas) where medicines are imaged, from each of the taken images obtained by the taken image obtaining unit 14. Because a plurality of medicines are packaged in the divided package TP, a plurality of medicine areas are detected from each taken image. By detecting the medicine areas, the areas to be processed can be limited, which can reduce the time required to the processes. Here, regarding the medicine areas of the same medicine, medicine area detected from the taken image through the camera 36A and a medicine area detected from the taken image through the camera 36B are associated with each other as a pair of medicine areas of the same medicine.

In step S4 (example of first image processing step, and example of first image processing function), the first image processing unit 18 performs the process of enhancing engraved mark portions of the medicines, based on at least one taken image among the taken images obtained by the taken image obtaining unit 14. Here, for each pair of medicine areas of the same medicine among the medicine areas detected in step S3, a corresponding pair of first enhanced images is generated. A plurality of pairs of first enhanced images thus generated, are input into the image integrating unit 22.

As the process of enhancing the engraved mark portion of the medicine, for example, three-dimensional information of the surfaces of each medicine is obtained by photometric stereo or the like, and the first enhanced images are generated. For example, contour extraction images that represent heights in grayscale (luminance) in the images, which are described in PTL 1, can be adopted as the first enhanced images. Here, the first enhanced images are represented to have high luminance values at portions of grooves of the engraved marks of the medicines.

In step S5 (example of second image processing step, and example of second image processing function), the second image processing unit 20 performs the process of enhancing the printed character portions of the medicines, based on at least one taken image among the taken images obtained by the taken image obtaining unit 14. Here, for each pair of medicine areas of the same medicine among the medicine areas detected in step S3, a corresponding pair of second enhanced images is generated. A plurality of pairs of second enhanced images thus generated, are input into the image integrating unit 22.

As the process of enhancing the printed character portion of the medicine, for example, at least one of a smoothing process for reducing the noise component, a sharpening process for enhancing the edge and an edge detecting process for removing the portions other than the printed character portion is applied to perform a binarizing process. Here, it is possible to use any of publicly known methods such as a process of adopting, as a pixel value, an absolute value of a difference from an average value of pixel values, a process of adopting, as a pixel value, a result of division by the average value of pixel values, a process of division by a blurred image, a process of applying a difference of local pixel values. Here, the second enhanced images are represented to have high luminance values at printed character portions of the medicines.

In step S6 (example of image integrating step, and example of image integrating function), the image integrating unit 22 compares luminance values of the first enhanced image and the second enhanced image generated from the same taken image at corresponding positions with each other, adopts the luminance values being relatively higher to generate an integrated image. Here, a pair of integrated images is generated from a pair of first enhanced images and a pair of second enhanced images generated from the same medicine area. A plurality of pairs of integrated images thus generated, are input into the determining unit 24.

In step S7 (example of master image obtaining step, and example of master image obtaining function), a pair of master images for one medicine among the medicines included in the prescription information obtained in step S1 is obtained. It may be possible to obtain reference images stored in the storage unit 40 as they are to adopt them as the master images. Alternatively, it may be possible to apply image processing such as enlargement or reduction, or brightness adjustment to the reference images to adopt them as the master images. As described above, a pair of master images exists for each medicine.

In step S8, the determining unit 24 selects a pair of integrated images among the pairs of integrated images generated in step S6.

In step S9, the similarity calculating unit 26 calculates the similarity between the pair of master images obtained in step S7 and the pair of integrated images selected in step S8. The similarity described here is calculated such that the greater the degree of the similarity is, the higher the value of the similarity is.

In step S10 (example of determining step, and example of determining function), the determining unit 24 determines whether or not the imaged medicine is the same as one of the medicines described in the prescription based on the similarity calculated in step S9. Here, if the similarity is higher than a predetermined threshold, they are determined to be the same.

Alternatively, it may be possible to calculate the similarities with all the integrated images for the pair of master images obtained in step S7, and then determine that, for integrated images having the highest similarity, the medicine in that integrated images is the same as a medicine in the master images.

In step S11, the processing unit 10 determines whether or not collation is completed for all the integrated images. If there are integrated images having not been collated yet, the processing returns to step S8, new integrated images are selected and analogous processes are repeated. If the collation is completed, the processing transitions to step S12.

In step S12, it is determined whether or not there is a medicine which is the same as (identical to) a medicine in the master images selected in step S7, that is, whether or not there is a medicine which is the same as one of medicines described in the prescription. If it is determined that there is no medicine which is the same as one of the medicines described in the prescription, the processing transitions to step S13. If it is determined that there is a medicine which is the same as one of the medicines described in the prescription, the processing transitions to step S14.

In step S13, the display unit 50 displays that there is no medicine which is the same as one of the medicines described in the prescription, on the monitor 52 (error indication), and the processing of this flowchart is finished.

In step S14, the processing unit 10 determines whether or not collation is completed for all the medicines described in the prescription (all the medicines included in the prescription information read in step S1). If there is any medicine having not been collated yet, the processing returns to step S7, a new pair of master images is obtained and analogous processes are repeated. If the collation is completed, the processing transitions to step S15.

In step S15, the processing unit 10 determines whether or not collation is completed for all the divided packages TP included in the strip medicine package PB. If there is a divided package TP which has not been collated yet, the processing returns to step S2, the strip medicine package PB is conveyed, taken images of a new divided package TP are obtained, and analogous processes are repeated. If the collation is completed for all the divided packages TP, the processing transitions to step S16.

In step S16, the display unit 50 displays that the audit result is normal (normal indication) on the monitor 52, and the processing of this flowchart is finished.

Figure 6:
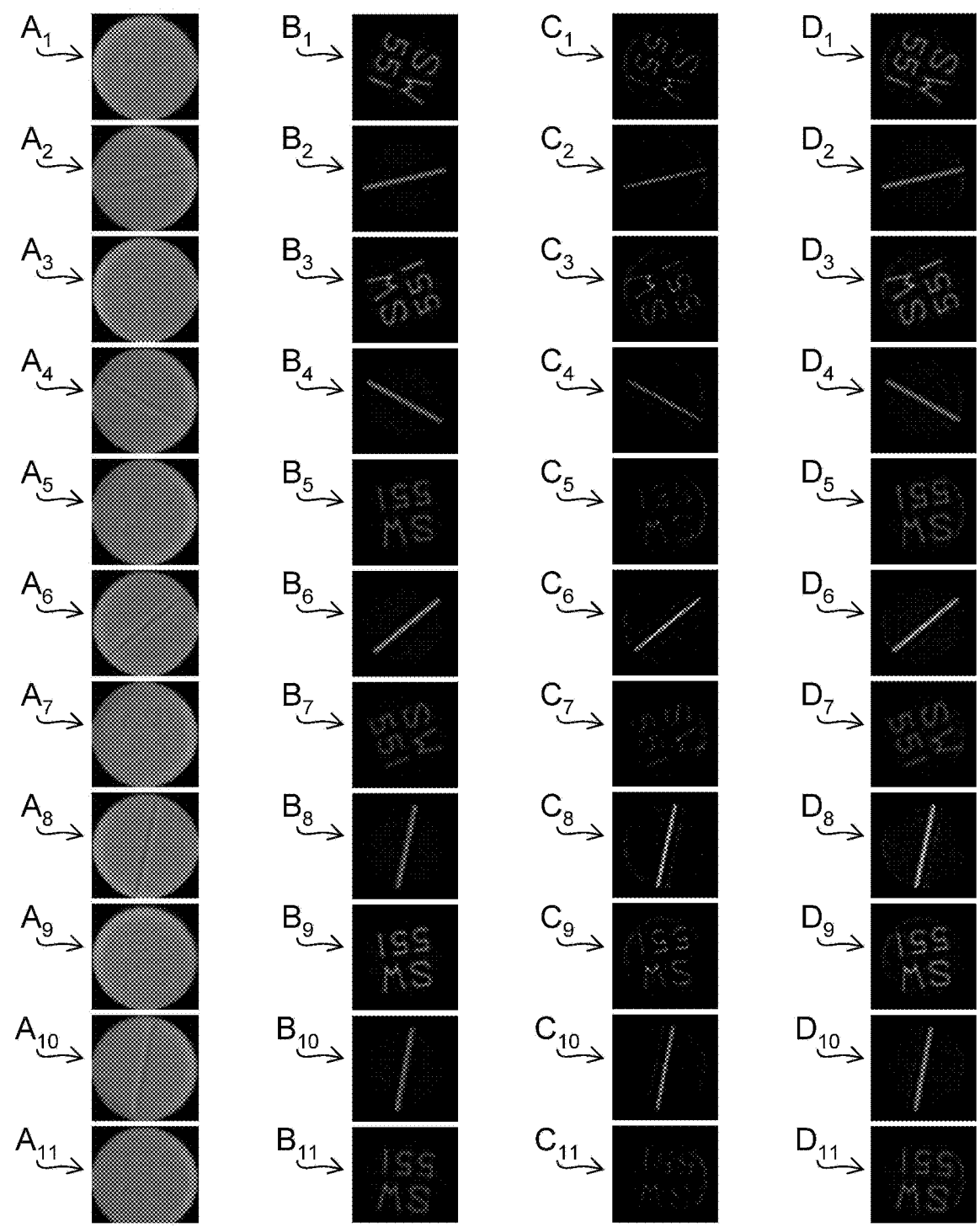
FIG. 6 shows an example of image processing results.
Figure 7:
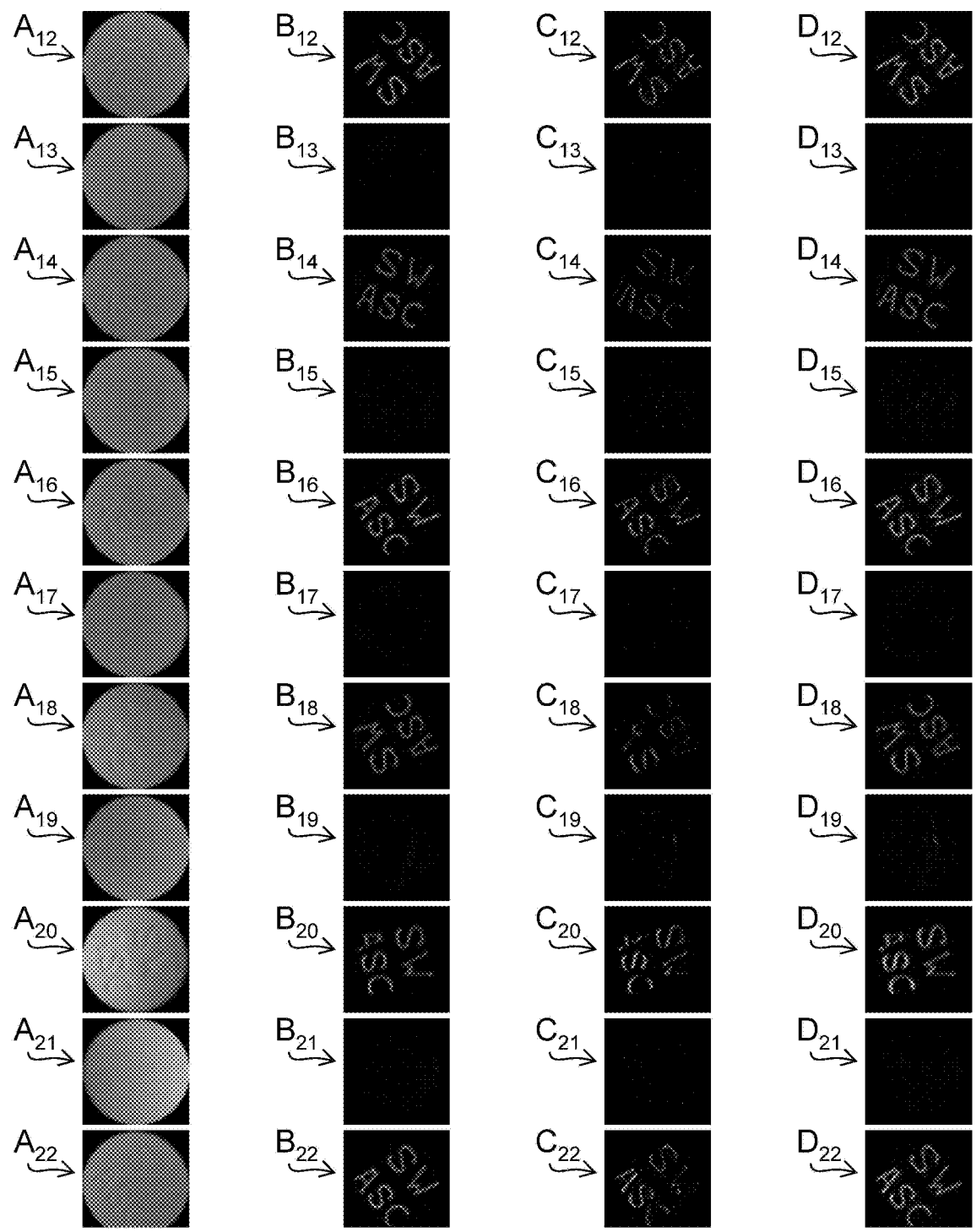
FIG. 7 shows an example of image processing results.

FIGS. 6 to 9 show examples of image processing results. Medicine areas $A_1$ to $A_{11}$ shown in FIG. 6 are examples of medicine areas detected from taken images of a medicine having an engraved mark on its surface. Likewise, medicine areas $A_{12}$ to $A_{22}$ shown in FIG. 7 are examples of medicine areas detected from taken images of a medicine having an engraved mark on its surface.

Figure 8:
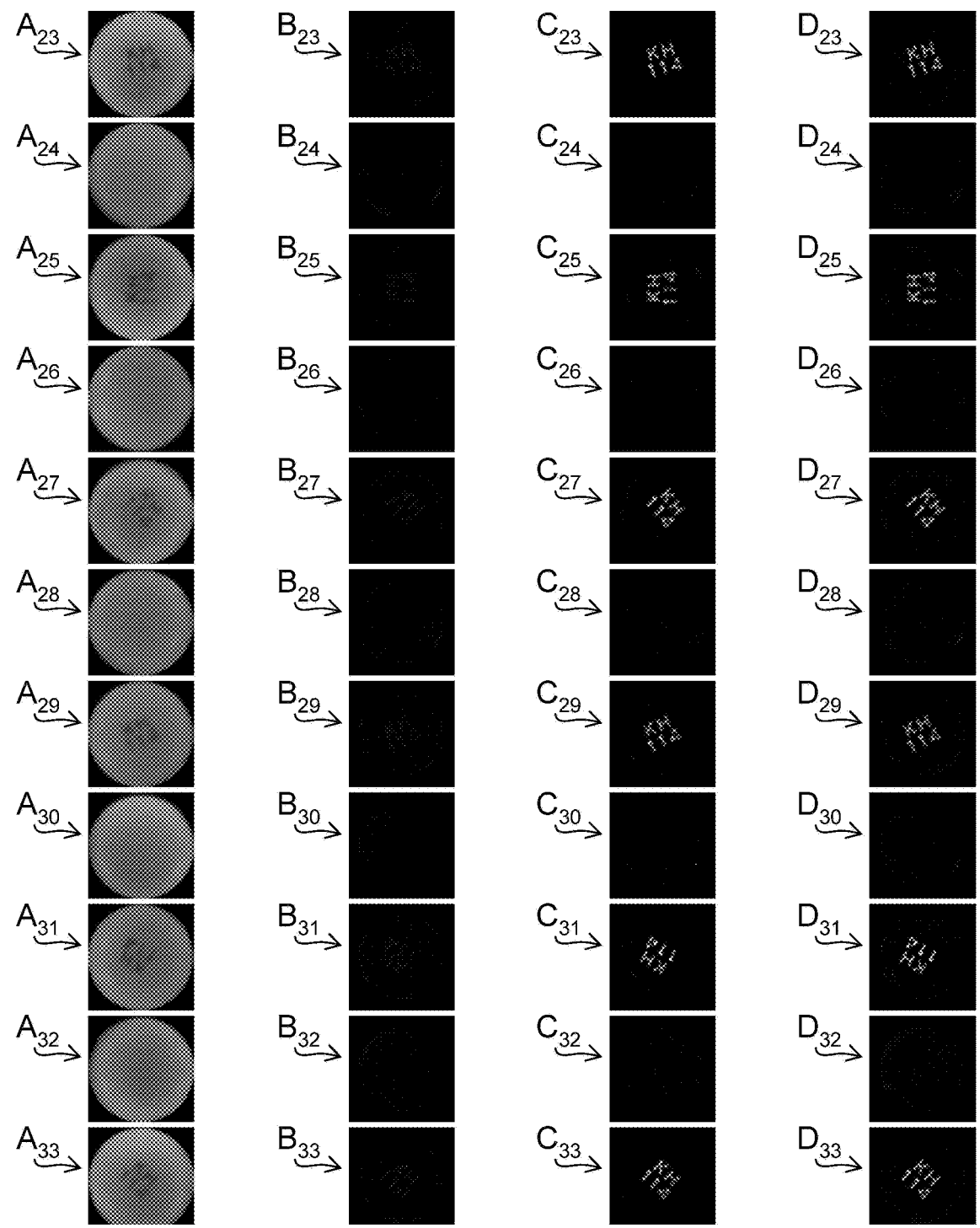
FIG. 8 shows an example of image processing results.
Figure 9:
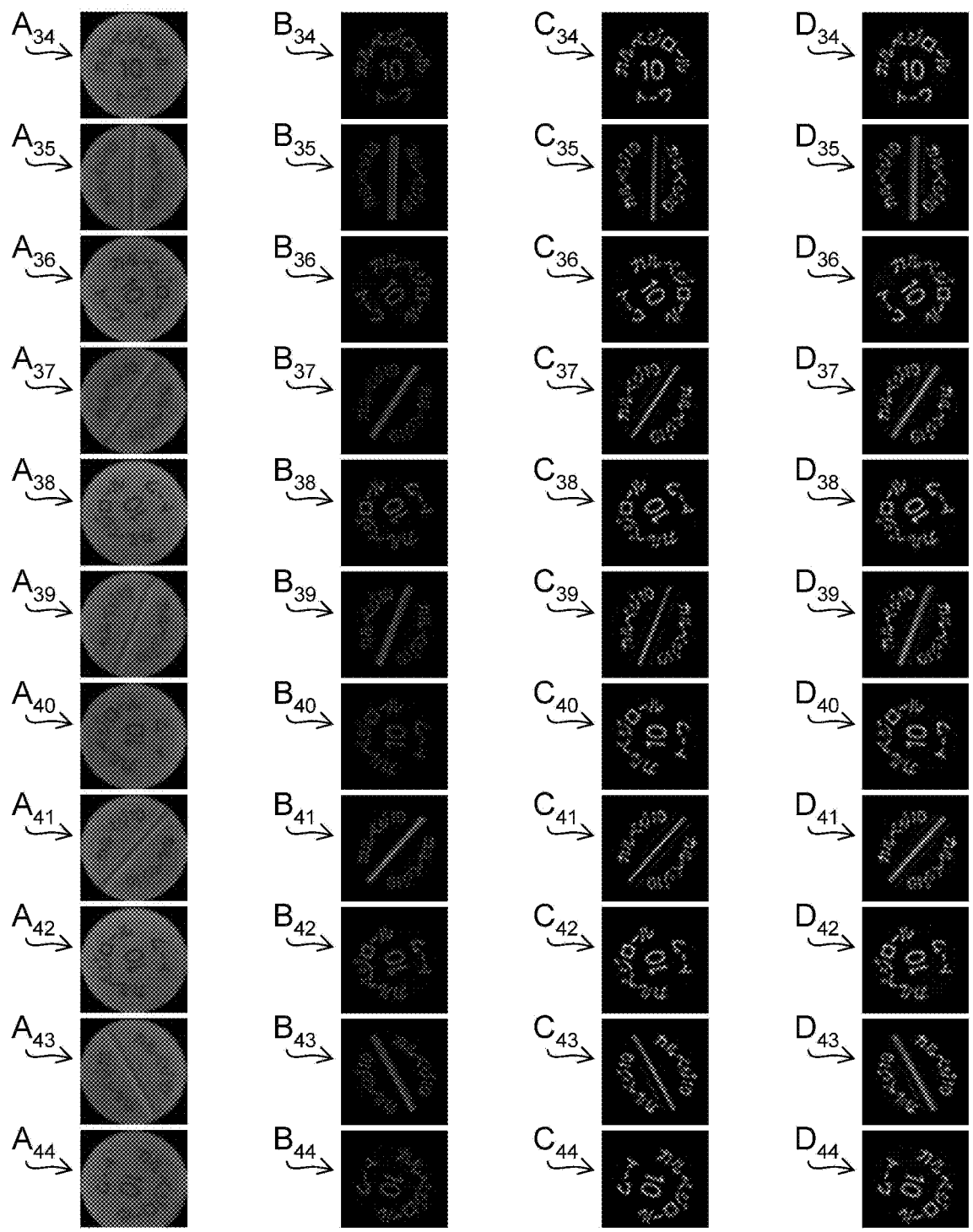
FIG. 9 shows an example of image processing results.

Medicine areas $A_{23}$ to $A_{33}$ shown in FIG. 8 are examples of medicine areas detected from taken images of a medicine having printed characters on its surface. Likewise, medicine areas $A_{34}$ to $A_{44}$ shown in FIG. 9 are examples of medicine areas detected from taken images of a medicine having printed characters on its surface.

Note that the taken images where the medicine areas $A_1$ to $A_{44}$ shown in FIGS. 6 to 9 are full-lighting images which are obtained in a state where all the light sources 34N, 34S, 34E and 34W are turned on. The medicine areas $A_1$ to $A_{44}$ include medicine areas obtained from taken images on one surface side of the medicine, and medicine areas obtained from taken images on the other surface side, in a mixed manner.

First enhanced images $B_1$ to $B_{44}$ shown in FIGS. 6 to 9 are examples of the first enhanced images respectively generated from the same areas as the medicine areas $A_1$ to $A_{44}$. Here are shown the first enhanced images generated based on medicine areas in four (example of three or more) taken images taken in a state where the light sources 34N, 34S, 34E and 34W are individually turned on.

Second enhanced images $C_1$ to $C_{44}$ shown in FIGS. 6 to 9 are examples of the second enhanced images generated from the respective medicine areas $A_1$ to $A_{44}$.

Integrated images $D_1$ to $D_{44}$ shown in FIGS. 6 to 9 are examples of integrated images generated from the first enhanced images $B_1$ to $B_{44}$ and the second enhanced images $C_1$ to $C_{44}$. For the medicines shown in FIGS. 6 and 7, the luminance values of the identification information are represented to be relatively larger (whiter) in the first enhanced images $B_1$ to $B_{22}$ than in the second enhanced images $C_1$ to $C_{22}$. Accordingly, the pixels of the first enhanced images $B_1$ to $B_{22}$ are mainly adopted as the integrated images.

On the other hand, for the medicines shown in FIGS. 8 and 9, the luminance values of the identification information are represented to be relatively larger in the second enhanced images $C_{23}$ to $C_{44}$ than in the first enhanced images $B_{23}$ to $B_{44}$. Accordingly, the pixels of the second enhanced images $C_{23}$ to $C_{44}$ are mainly adopted as the integrated images.

In this embodiment, the first image processing unit 18 performs the process of increasing the luminance value of the engraved mark portion of the medicine, the second image processing unit 20 performs the process of increasing the luminance value of the printed character portion of the medicine, the image integrating unit 22 compares the luminance values of the first enhanced image and the second enhanced image at corresponding positions, and adopts the luminance value of a higher luminance. In the case where the luminance value of the identification information in the master image is represented to be relatively lower than the values of the other portions, the first image processing unit 18 may perform the process of reducing the luminance values of the engraved mark portion of the medicine, the second image processing unit 20 may perform the process of reducing the luminance values of the printed character portion of the medicine, and the image integrating unit 22 may compare the luminance values of the first enhanced image and the second enhanced image at corresponding positions, and adopt the luminance value of a lower luminance.

In this embodiment, the first enhanced image and the second enhanced image are generated for the areas detected by the medicine detecting unit 16. Alternatively, it may be possible to generate the first enhanced images and the second enhanced images for the taken images, and then detect the medicine areas.

As described above, the process of enhancing the engraved mark portion of the medicine is performed to generate the first enhanced images, and the process of enhancing the printed character portion of the medicine to generate the second enhanced images, the first enhanced images and the second enhanced images are integrated to generate the integrated images, and the integrated images are used for collation with the master images. Accordingly, irrespective of whether the identification information added to the medicine is the engraved mark or the printed character, the identification information can be appropriately recognized, and correct collation can be achieved.

Second Embodiment

Figure 10:
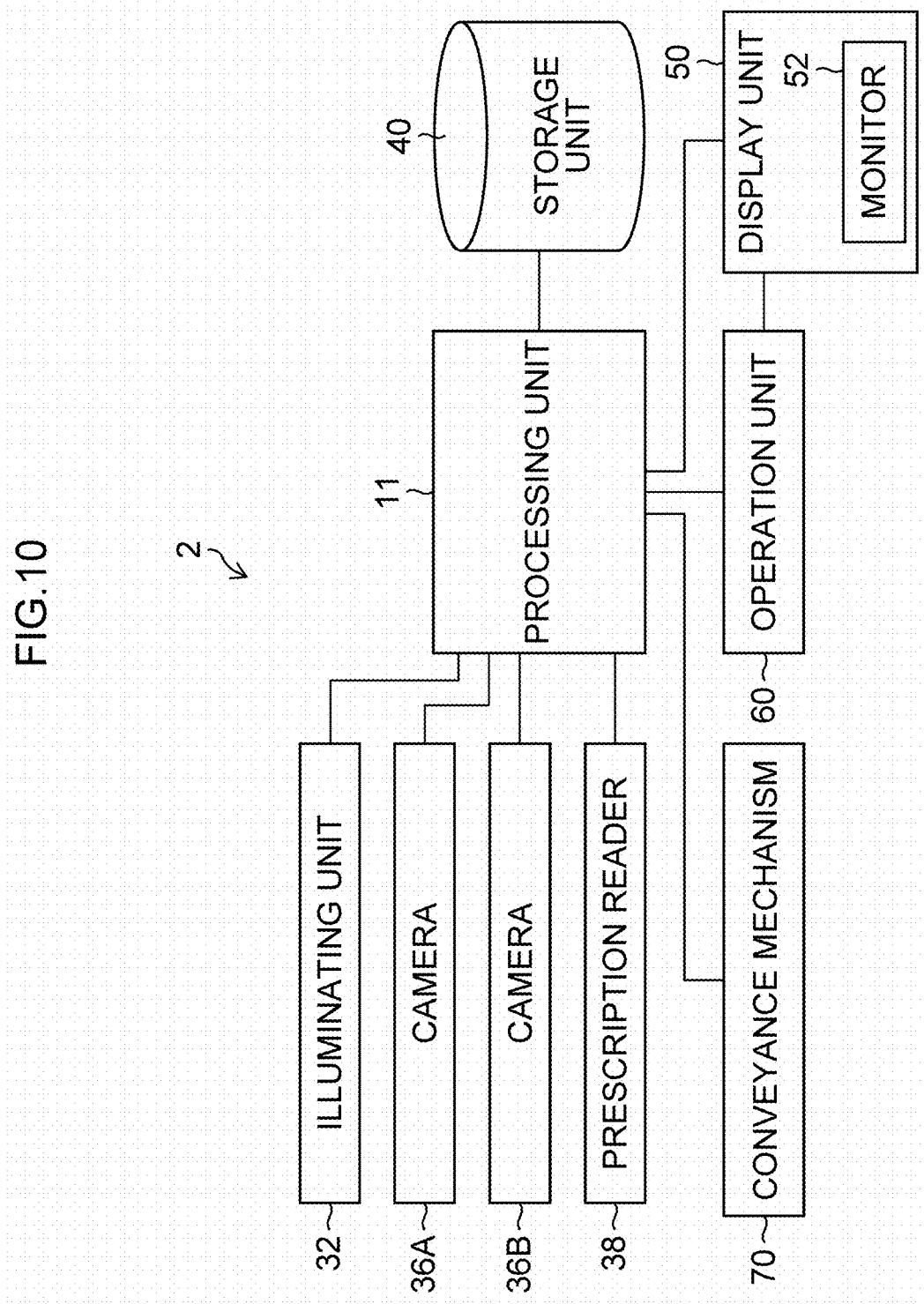
FIG. 10 shows a configuration of a medicine inspection assistance device.

FIG. 10 shows the configuration of a medicine inspection assistance device 2 according to a second embodiment. Note that the parts common to those of the medicine inspection assistance device 1 shown in FIG. 1 are assigned the same numerals or characters; their detailed description is omitted. The medicine inspection assistance device 2 includes a processing unit 11. An illuminating unit 32, a camera 36A, a camera 36B, and a prescription reader 38 are connected to the processing unit 11.

The illuminating unit 32 includes a plurality of light sources 34. The arrangement of the light sources 34, the camera 36A and the camera 36B is analogous to that of the medicine inspection assistance device 1 shown in FIGS. 2 and 3.

[Configuration of Processing Unit]

Figure 11:
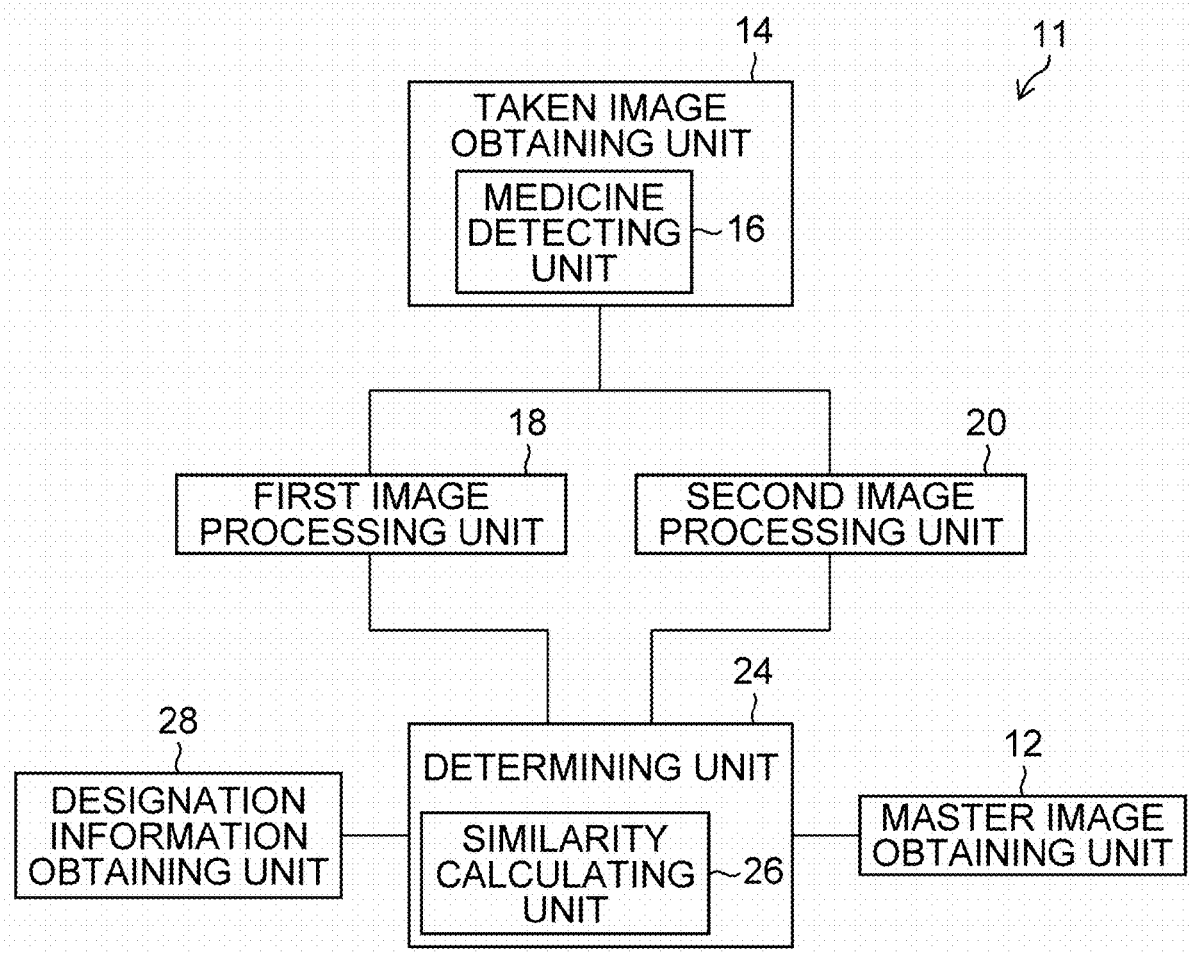
FIG. 11 shows an internal configuration of a processing unit.

FIG. 11 shows the internal configuration of the processing unit 11 (example of image processing device). Note that the parts common to those of the processing unit 10 shown in FIG. 4 are assigned the same numerals or characters; their detailed description is omitted. As shown in FIG. 11, the processing unit 11 includes a designation information obtaining unit 28.

Designation information is information that designates, on a medicine-by-medicine basis, which one of the first enhanced image generated by the first image processing unit 18 and the second enhanced image generated by the second image processing unit 20 is to be used for collation.

In a case where identification information has been added to a medicine with mark engraving, discrimination of the identification information is facilitated by using the first enhanced images obtained by applying the process of enhancing the engraved mark portion of the medicine. Accordingly, the designation information associated with the master image of the medicine having the engraved mark designates the first enhanced images as the collation target images to be used for collation. In a case where identification information has been added to a medicine with character printing, discrimination of the identification information is facilitated by using the second enhanced images obtained by applying the process of enhancing the printed character portion of the medicine. Accordingly, the designation information associated with the master image of the medicine having the printed character designates the second enhanced images as the collation target images to be used for collation.

The designation information is stored in the storage unit 40 in association with the information on the medicine, such as the master images. The designation information obtaining unit 28 reads and obtains the designation information on the prescribed medicine from the storage unit 40 based on the prescription information obtained from the prescription reader 38.

The first enhanced images generated by the first image processing unit 18 and the second enhanced images generated by the second image processing unit 20 are input into the determining unit 24. The determining unit 24 selects either the first enhanced images or the second enhanced images as the collation target images based on the designation information obtained by the designation information obtaining unit 28. The determining unit 24 collates the selected collation target images with the master images obtained by the master image obtaining unit 12, and determines whether or not the medicines packaged in the divided package TP are the same as the medicines to be dispensed in accordance with the prescription.

[Processes of Medicine Inspection Assistance Method]

Figure 12:
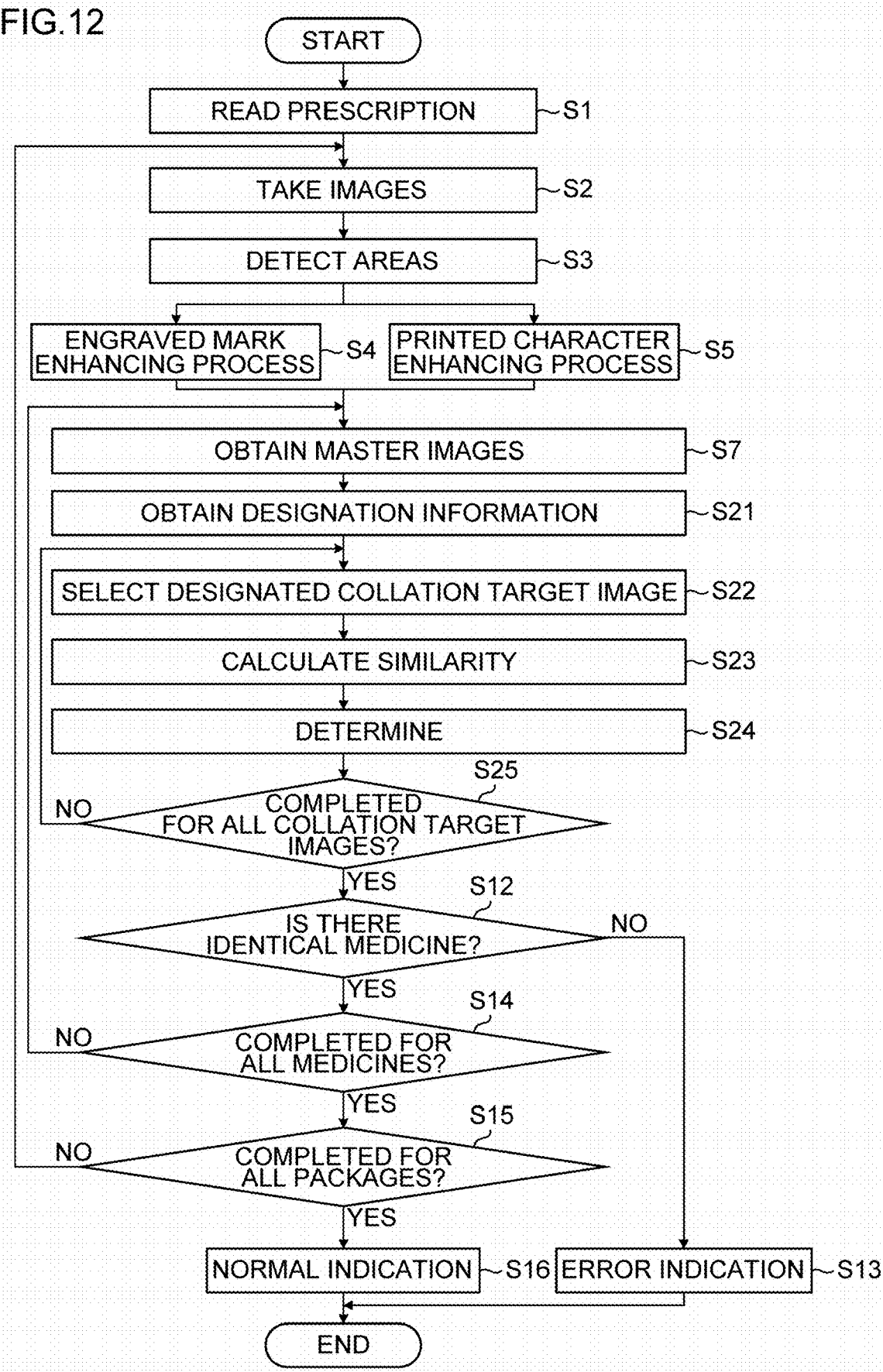
FIG. 12 is a flowchart showing processes of a medicine inspection assistance method.

A medicine inspection assistance method (example of image processing method) by the medicine inspection assistance device 2 is described. FIG. 12 is a flowchart showing the processes of the medicine inspection assistance method. Note that the parts common to those of the flowchart shown in FIG. 5 are assigned the same numerals or characters; their detailed description is omitted.

In step S1, the prescription information is obtained.

In step S2 (example of taken image obtaining step, and example of taken image obtaining function), for each of the upper side and the lower side of a divided package TP, taken images are obtained. The obtained taken images include images respectively taken in four illumination directions different from each other and a full-lighting image taken while irradiating from all the four directions.

In step S3, the medicine areas are detected from each of the taken images. Here, a medicine area detected from the taken image through the camera 36A and a medicine area detected from the taken image through the camera 36B, which are medicine areas of the same one medicine, are detected as a pair of medicine areas of the same medicine and associated with each other.

In step S4 (example of first image processing step, and example of first image processing function), the process of enhancing the engraved mark portion of the medicine is performed to generate the first enhanced image of each medicine area. The first image processing unit 18 generates a pair of first enhanced images for the pair of the medicine areas of the same medicine. Here, the first enhanced images are represented to have high luminance values at a portion of a groove of the engraved mark of the medicine. The plurality of pairs of first enhanced images thus generated, are input into the determining unit 24.

In step S5 (example of second image processing step, and example of second image processing function), the process of enhancing the printed character portion of the medicine is performed to generate the second enhanced image of each medicine area. The second image processing unit 20 generates a pair of second enhanced images for the pair of the medicine areas of the same medicine. Here, the second enhanced images are represented to have high luminance values at a printed character portion of the medicine. The plurality of pairs of second enhanced images thus generated, are input into the determining unit 24.

In step S7 (example of master image obtaining step, and example of master image obtaining function), a pair of master images of one medicine among the medicines included in the prescription information obtained in step S1 is obtained. The master images are represented to have relatively high luminance value of the identification information in comparison with the values of the other portions.

In step S21, the designation information obtaining unit 28 obtains the designation information associated with the master images obtained in step S7, from the storage unit 40. The designation information designates either the first enhanced images or the second enhanced images.

In step S22, the determining unit 24 selects the images designated by the designation information input from the designation information obtaining unit 28, between the first enhanced images and the second enhanced images of the medicine to be collated. That is, if the designation information designates the first enhanced images, the pair of first enhanced images is selected as the pair of collation target images (images to be collated); if the designation information designates the second enhanced images, the pair of second enhanced images is selected as the pair of collation target images. Note that in a case where an engraved mark is added on one surface of the medicine and a printed character is added on the other surface, the designation information may designate both the first enhanced images and the second enhanced images. In this case, it may be possible to appropriately select a required first enhanced image and a second enhanced image from the pair of first enhanced images and the pair of second enhanced images.

In step S23, the similarity calculating unit 26 calculates the similarity indicating the degree at which the pair of master images obtained in step S7 and the pair of collation target images selected in step S22 are similar to each other. The similarity described here is calculated such that the greater the degree of the similarity is, the higher the value of the similarity is.

In step S24 (example of determining step, and example of determining function), the determining unit 24 determines whether or not the imaged medicine is the same as one of the medicines described in the prescription based on the similarity calculated in step S23. Here, if the similarity is higher than a predetermined threshold, they are determined to be the same.

In step S25, the processing unit 10 determines whether or not collation is completed for all the collation target images. If there are integrated images having not been collated yet, the processing returns to step S22, new collation target images are selected and analogous processes are repeated. If the collation is completed, the processing transitions to step S12.

In step S12, it is determined whether or not there is a medicine which is the same as (identical to) a medicine in the master images selected in step S7, that is, whether or not there is a medicine which is the same as one of the medicines described in the prescription. If it is determined that there is no medicine which is the same as one of the medicines described in the prescription, the processing transitions to step S13. If it is determined that there is a medicine which is the same as one of the medicines described in the prescription, the processing transitions to step S14.

In step S13, the display unit 50 displays that there is no medicine which is the same as one of the medicines described in the prescription, on the monitor 52 (error indication), and the processing of this flowchart is finished.

In step S14, the processing unit 10 determines whether or not collation is completed for all the medicines described in the prescription (all the medicines included in the prescription information read in step S1). If there is any medicine having not been collated yet, the processing returns to step S7, new master images are obtained and analogous processes are repeated. If the collation is completed, the processing transitions to step S15.

In step S15, the processing unit 10 determines whether or not collation is completed for all the divided packages TP included in the strip medicine package PB. If there is a divided package TP which has not been collated yet, the processing returns to step S2, the strip medicine package PB is conveyed, taken images of a new divided package TP are obtained, and analogous processes are repeated. If the collation is completed, the processing transitions to step S16.

In step S16, the display unit 50 displays that the audit result is normal (normal indication) on the monitor 52, and the processing of this flowchart is finished.

The medicines shown in FIGS. 6 and 7 have engraved marks added thereto. The designation information associated with each master image of the medicine designates the first enhanced images. Accordingly, for collation of the master images relating to the medicine areas $A_1$ to $A_{22}$, the respective first enhanced images $B_1$ to $B_{22}$ are selected.

Meanwhile, the medicines shown in FIGS. 8 and 9 have printed characters added thereto. The designation information associated with each master image of the medicine designates the second enhanced images. Accordingly, for collation of the master images relating to the medicine areas $A_{23}$ to $A_{44}$, the respective second enhanced images $C_{23}$ to $C_{44}$ are selected.

In this embodiment, the first image processing unit 18 performs the process of increasing the luminance value of the engraved mark portion of the medicine, and the second image processing unit 20 performs the process of increasing the luminance value of the printed character portion of the medicine. In a case where the luminance value of the identification information in the master image is represented to be low relatively to the values of the other portions, it may be possible to perform the process of reducing the luminance value of the engraved mark portion of the medicine by the first image processing unit 18, and perform the process of reducing the luminance value of the printed character portion of the medicine by the second image processing unit 20.

As described above, the process of enhancing the engraved mark portion of the medicine is performed to generate the first enhanced images, and the process of enhancing the printed character portion of the medicine is performed to generate the second enhanced images, the designation information designating either the first enhanced images or the second enhanced images as images to be used for collation is obtained, and the images designated by the designation information are collated with the master images. Accordingly, irrespective of whether the identification information added to the medicine is the engraved mark or the printed character, the identification information can be appropriately recognized, and correct collation can be achieved.

Here, the designation information designates either the first enhanced images or the second enhanced images as images to be used for collation. Alternatively, it may be possible to determine whether the identification information is added by mark engraving or by character printing by analyzing the taken images or analyzing the first enhanced images and the second enhanced images, and then designate the images to be used for collation according to the determination result.

For example, the first enhanced images are compared with the second enhanced images. In a case where the luminance value of the identification information in the first enhanced images are higher, it can be determined that the identification information has been added by mark engraving. In a case where the luminance value of the identification information in the second enhanced images is higher, it can be determined that the identification information has been added by character printing.

Alternatively, it may be possible to analyze a correlation between the images respectively taken with four illumination directions different from each other, and then determine that the identification information has been added by mark engraving in a case where the correlation between the images is low, and determine that the identification information has been added by character printing in case where the correlation between the images is high.

Third Embodiment

[Processes of Medicine Inspection Assistance Method]

Figure 13:
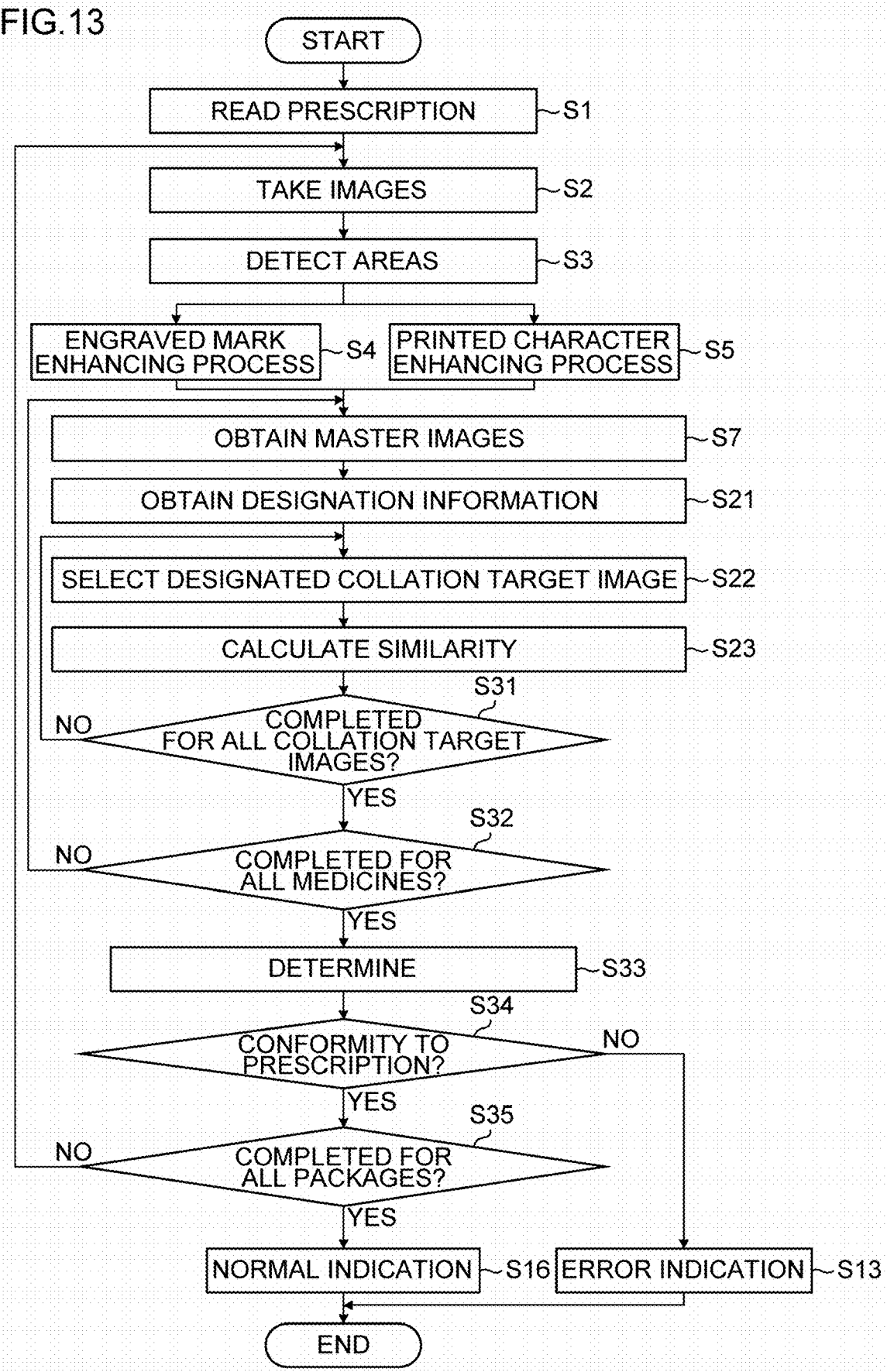
FIG. 13 is a flowchart showing processes of a medicine inspection assistance method.

FIG. 13 is a flowchart showing processes of a medicine inspection assistance method according to a third embodiment. Note that the parts common to those of the flowchart shown in FIG. 12 are assigned the same numerals or characters; their detailed description is omitted.

Steps S1 to S5 are analogous to those of the second embodiment. That is, the prescription information is obtained. The medicines packaged in a divided package TP of the strip medicine package PB are imaged to obtain a plurality of taken images. Medicine areas where the medicines are imaged are detected from the taken images. The first enhanced images where the engraved mark portions of the medicines are enhanced, and the second enhanced images where the printed character portions of the medicines are enhanced are generated.

In step S7, a pair of master images is obtained. In step S21, the designation information associated with the master images is obtained. Furthermore, in step S22, images designated by the designation information are selected from between the first enhanced images and the second enhanced images of the medicine to be collated.

In step S23, the similarity between the pair of master images obtained in step S7 and the pair of collation target images selected in step S22 is calculated. The similarity described here is calculated such that the greater the degree of the similarity is, the higher the value of the similarity is.

Next, in step S31, the processing unit 10 determines whether or not calculation of the similarity is completed for the combinations of all the collation target images with the master images obtained in step S7. If there is any collation target image whose similarity has not been calculated yet, the processing returns to step S22, a new pair of collation target images is selected and analogous processes are repeated. Accordingly, for the master images obtained in step S7, the similarities of the combinations with all the collation target images can be calculated. If the similarity calculation for the combinations with all the collation target images has been completed, the processing transitions to step S32.

Subsequently, in step S32, the processing unit 10 determines whether similarity calculation for all the medicines described in the prescription (all the medicines included in the prescription information read in step S1) is completed or not. If there is any medicine whose similarity calculation has not been completed yet, the processing returns to step S7, a new pair of master images is obtained and analogous processes are repeated. Accordingly, it is possible to calculate, for every master image, the similarities of the combinations with all the collation target images obtained in step S22. If the similarity calculation for all the master images has been completed, the processing transitions to step S33.

In step S33 (example of determining step, and example of determining function), the determining unit 24 determines whether or not the imaged medicines are the same as the medicines described in the prescription based on the similarities of all the combinations between the master images and the collation target images calculated in step S23.

For example, for the four collation target images of the collation target image (1), the collation target image (2), the collation target image (3) and the collation target image (4), and the four master images of the master image (A), the master image (B), the master image (C) and the master image (D), it is assumed that the similarity (1A), the similarity (1B), the similarity (1C), the similarity (1D), the similarity (2A), the similarity (2B), . . . , the similarity (4C) and the similarity (4D) have been calculated for respective combinations.

Here, provided that the highest similarity among the similarities (1A, 1B, 1C and 1D) pertaining to the collation target image (1) is the similarity (1B), and the highest similarity among the similarities (1B, 2B, 3B and 4B) pertaining to the master image (B) is the similarity (1B), the determining unit 24 determines that the medicine indicated by the collation target image (1) is the medicine indicated by the master image (B).

Subsequently, the determining unit 24 excludes the collation target image (1) and the master image (B) from the collation targets, selects combinations having high similarities in an analogous manner, and determines combinations between the medicines described in the prescription and the imaged medicines.

In step S34, it is determined whether or not the medicines packaged in the divided package TP are as described in the prescription, from the determination result in step S33. If it is determined that the medicines do not conform to the prescription, the processing transitions to step S13. If it is determined that the medicines conform to the prescription, the processing transitions to step S35.

In step S13, the display unit 50 displays the error indication on the monitor 52, and the processing of this flowchart is finished.

In step S35, the processing unit 10 determines whether or not collation is completed for all the divided packages TP included in the strip medicine package PB. If there is any divided package TP having not been collated yet, the processing returns to step S2, the strip medicine package PB is conveyed, taken images of a new divided package TP are obtained, and analogous processes are repeated. If the collation is completed, the processing transitions to step S16.

In step S16, the display unit 50 displays the normal indication on the monitor 52, and the processing of this flowchart is finished.

As described above, the relative relationship of the similarities is used to determine the combination of the medicines to be dispensed and the dispensed medicines. Accordingly, it can be determined whether or not the medicines to be dispensed are the same as the dispensed medicines, for all the imaged medicines.

Likewise, it may be possible to determine whether or not the imaged medicines are the same as the medicines described the prescription in the first embodiment, based on the relative relationship of the similarities of all the combinations of the master images and the integrated images.

<Other>

The image processing method described above can be configured as a program of causing a computer to achieve the master image obtaining function, the taken image obtaining function, the first image processing function, the second image processing function, the image integrating function, the designation information obtaining function, and the determining function. Further, the image processing method described above can be configured as a non-transitory recording medium such as a CD-ROM (Compact Disk-Read Only Memory), storing the program.

In the thus described embodiments, for example, the hardware structure of the processing unit that executes various kinds of processes, such as of the processing unit 10 and the processing unit 11, is any of various processors as described below. The various processors include: a CPU (Central Processing Unit), which is a general-purpose processor executing software (program) to function as various processing units; a programmable logic device (PLD), such as an FPGA (Field Programmable Gate Array), which is a processor whose circuit configuration can be changed after production; and dedicated circuitry, such as an ASIC (Application Specific Integrated Circuit), which is a processor having a circuit configuration designed in a dedicated manner to execute a specific process.

One processing unit may include one among these various processors, or include the same kind or different kinds of two or more processors (e.g., multiple FPGAs or a combination of a CPU and an FPGA). Alternatively, multiple processing units may be made up of a single processor. Examples where multiple processing units are made up of a single processor include, firstly, a mode in which, as typified by a computer such as a server and a client, a combination of one or more CPUs and software constitute a single processor, and the processor functions as multiple processing units. Secondly, as typified by a system on chip (SoC), the examples include a mode of using a processor which realizes the function of the entire system including multiple processing units with a single IC (Integrated Circuit) chip. As described above, various processing units are configured using one or more various processors as a hardware configuration.

Furthermore, more specifically, each of the hardware structures of these various processors is circuitry including combined circuit elements such as semiconductor elements.

The technical scope of the present invention is not limited to the scope described in the above embodiments. The configurations and the like in the respective embodiments can be appropriately combined between the embodiments in a range without departing from the spirit of the present invention.

REFERENCE SIGNS LIST

1 Medicine inspection assistance device
2 Medicine inspection assistance device
10 Processing unit
11 Processing unit
12 Master image obtaining unit
14 Taken image obtaining unit
16 Medicine detecting unit
18 First image processing unit
20 Second image processing unit
22 Image integrating unit
24 Determining unit
26 Similarity calculating unit
28 Designation information obtaining unit
32 Illuminating unit
34 Light sources
34E Light sources
34N Light sources
34S Light sources
34W Light sources
36A Camera
36B Camera
38 Prescription reader
40 Storage unit
50 Display unit
52 Monitor
60 Operation unit
70 Conveyance mechanism
A1 to A44 Medicine area
B1 to B44 First enhanced image
C1 to C44 Second enhanced image
D1 to D44 Integrated image
PA Imaging optical axis
PB Strip medicine package
TP Divided package
S1 to S35 Steps of medicine inspection assistance method in medicine inspection assistance device

What is claimed is:

1. An image processing device, comprising a processor configured to:
obtain a master image of a medicine to be dispensed based on prescription information;
obtain a plurality of taken images of a dispensed medicine, with emitting directions of light to a surface of the dispensed medicine different from each other;
enhance an engraved mark portion of at least one of the obtained taken images, and generate a first enhanced image of the dispensed medicine;
enhance a printed character portion of at least one of the obtained taken images, and generate a second enhanced image of the dispensed medicine;
integrate the first enhanced image and the second enhanced image with each other to generate an integrated image of the dispensed medicine; and
collate the generated integrated image of the dispensed medicine with the obtained master image, and determine whether the medicine to be dispensed is identical to the dispensed medicine or not,
wherein the processor is further configured to:
increase a luminance value at the engraved mark portion of the at least one of the obtained taken images to generate the first enhanced image,
increase a luminance value at the printed character portion of the at least one of the obtained taken images to generate the second enhanced image, and
compare the luminance value of the first enhanced image and the luminance value of the second enhanced image at corresponding positions with each other, and adopt the luminance value of a higher luminance to generate the integrated image of the dispensed medicine.

2. The image processing device according to claim 1, wherein the processor is further configured to:
detect an area where the medicine is imaged, from each of the taken images, and
respectively enhance the engraved mark portion and the printed character portion, for the detected area, to generate the first enhanced image and the second enhanced image.

3. The image processing device according to claim 1, wherein the processor is configured to:
obtain three or more taken images of the dispensed medicine, and
generate the first enhanced image, based on the three or more obtained taken images.

4. The image processing device according to claim 1, wherein the processor is configured to obtain three-dimensional information of the surface of the dispensed medicine by photometric stereo, and use the obtained three-dimensional information to generate the first enhanced image.

5. The image processing device according to claim 1, wherein the processor is configured to perform at least one of a smoothing process, a sharpening process and an edge detecting process, to generate the second enhanced image.

6. The image processing device according to claim 1,
wherein the engraved mark portion of at least one of the obtained taken images is enhanced by a first enhancement process;
wherein the printed character portion of at least one of the obtained taken images is enhanced by a second enhancement process; and
wherein the first enhancement process is different than the second enhancement process.

7. An image processing device, comprising a processor configured to:
obtain a master image of a medicine to be dispensed based on prescription information,
obtain a plurality of taken images of a dispensed medicine, with emitting directions of light to a surface of the dispensed medicine different from each other,
enhance an engraved mark portion of at least one of the obtained taken images and generate a first enhanced image of the dispensed medicine;
enhance a printed character portion of at least one of the obtained taken images, and generate a second enhanced image of the dispensed medicine:
integrate the first enhanced image and the second enhanced image with each other to generate an integrated image of the dispensed medicine; and
collate the generated integrated image of the dispensed medicine with the obtained master image, and determine whether the medicine to be dispensed is identical to the dispensed medicine or not,
wherein the processor is further configured to:
reduce a luminance value at the engraved mark portion of the at feast one of the obtained taken images to generate the first enhanced image,
reduce a luminance value at the printed character portion of the at least one of the obtained taken images to generate the second enhanced image, and
compare the luminance value of the first enhanced image and the luminance value of the second enhanced image at corresponding positions with each other, and adopt the luminance value of a lower luminance to generate the integrated image of the dispensed medicine.

8. An image processing device, comprising a processor configured to:
obtain a master image of a medicine to be dispensed based on prescription information;
obtain a plurality of taken images of a dispensed medicine, with emitting directions of light to a surface of the dispensed medicine different from each other;
enhance an engraved mark portion of at least one of the obtained taken images, and generate a first enhanced image of the dispensed medicine;
enhance a printed character portion of at least one of the obtained taken images, and generate a second enhanced image of the dispensed medicine;
integrate the first enhanced image and the second enhanced image with each other to generate an integrated image of the dispensed medicine; and
collate the generated integrated image of the dispensed medicine with the obtained master image, and determine whether the medicine to be dispensed is identical to the dispensed medicine or not,
wherein the processor is further configured to:
calculate a similarity indicating a degree at which the generated integrated image of the dispensed medicine is similar to the obtained master image, and
determine whether the medicine to be dispensed is identical to the dispensed medicine or not, based on the calculated similarity, and
wherein the processor is further configured to:
calculate similarities between a plurality of the generated integrated images of the dispensed medicine and a plurality of the obtained master images, and
determine that the medicine to be dispensed is identical to the dispensed medicine, for a combination of the generated integrated image of the dispensed medicine and the obtained master image with a highest similarity.

9. A medicine inspection assistance device, comprising:
a plurality of light sources configured to irradiate a surface of a dispensed medicine with light in a plurality of illumination directions different from each other;
an imager configured to image the dispensed medicine; and
a processor configured to:
obtain prescription information;
obtain a master image of a medicine to be dispensed, based on the prescription information;
control the light sources and the imager to obtain a plurality of taken images of the dispensed medicine, with illumination directions of light to the dispensed medicine different from each other;
enhance an engraved mark portion of at least one of the obtained taken images, and generate a first enhanced image of the dispensed medicine;
enhance a printed character portion of at least one of the Obtained taken images, and generate a second enhanced image of the dispensed medicine;
integrate the first enhanced image and the second enhanced image with each other to generate an integrated image of the dispensed medicine; and
collate the generated integrated image of the dispensed medicine with the obtained master image, and determine whether the medicine to be dispensed is identical to the dispensed medicine or not,
wherein the processor is further configured to:
increase a luminance value at the engraved mark portion of the at least one of the obtained taken images to generate the first enhanced image,
increase a luminance value at the printed character portion of the at least one of the obtained taken images to generate the second enhanced image, and
compare the luminance value of the first enhanced image and the luminance value of the second enhanced image at corresponding positions with each other, and adopt the luminance value of a higher luminance to generate the integrated image of the dispensed medicine.

10. The medicine inspection assistance device according to claim 9, wherein the processor is configured to obtain the taken images of the dispensed medicine irradiated with light by two or more light sources among the plurality of light sources.

11. The medicine inspection assistance device according to claim 9,
wherein the plurality of light sources irradiate a front side and a rear side of the dispensed medicine with light, and
the imager images the front side and the rear de of the dispensed medicine.

12. The medicine inspection assistance device according to claim 9,
wherein the plurality of light sources include a first light source configured to emit light in a first direction, a second light source configured to emit light in a second direction, a third light source configured to emit light in a third direction, and a fourth light source configured to emit light in a fourth direction, and
the second direction is a direction opposite to the first direction in plan view of the surface, the third direction is a direction orthogonal to the first direction in plan view of the surface, and the fourth direction is a direction opposite to the third direction in plan view of the surface.

13. An image processing method, comprising:
a master image obtaining step of obtaining a master image of a medicine to be dispensed, based on prescription information;
a taken image obtaining step of obtaining a plurality of taken images of a dispensed medicine, with emitting directions of light to a surface of the dispensed medicine different from each other;
a first image processing step of enhancing an engraved mark portion of at least one of the obtained taken images, and generating a first enhanced image of the dispensed medicine;
a second image processing step of enhancing a printed character portion of at least one of the obtained taken images, and generating a second enhanced image of the dispensed medicine;
an image integrating step of integrating the first enhanced image and the second enhanced image with each other to generate an integrated image of the dispensed medicine; and
a determining step of collating the generated integrated image of the dispensed medicine with the obtained master image, and determining whether the medicine to be dispensed is identical to the dispensed medicine or not,
wherein the image processing method further comprises:
a first luminance value increasing step of increasing a luminance value at the engraved mark portion of the at least one of the obtained taken images to generate the first enhanced image,
a second luminance value increasing step of increasing a luminance value at the printed character portion of the at least one of the obtained taken images to generate the second enhanced image, and
a comparing step of comparing the luminance value of the first enhanced image and the luminance value of the second enhanced image at corresponding positions with each other, and adopting the luminance value of a higher luminance to generate the integrated image of the dispensed medicine.

14. A non-transitory computer-readable storage medium wherein when an instruction stored in the recording medium is read by a computer, the instruction causes the computer to execute:
a master image obtaining function of obtaining a master image of a medicine to be dispensed, based on prescription information;
a taken image obtaining function of obtaining a plurality of taken images of a dispensed medicine with emitting directions of light to a surface of the dispensed medicine different from each other;
a first image processing function of enhancing an engraved mark portion of at least one of the obtained taken images, and generating a first enhanced image of the dispensed medicine;
a second image processing function of enhancing a printed character portion of at least one of the obtained taken images, and generating a second enhanced image of the dispensed medicine;
an image integrating function of integrating the first enhanced image and the second enhanced image with each other to generate an integrated image of the dispensed medicine; and
a determining function of collating the generated integrated image of the dispensed medicine with the obtained master image, and determining whether the medicine to be dispensed is identical to the dispensed medicine or not;
wherein the instruction causes the computer to further execute:
a first luminance value increasing function of increasing a luminance value at the engraved mark portion of the at least one of the obtained taken images to generate the first enhanced image,
a second luminance value increasing function of increasing a luminance value at the printed character portion of the at least one of the obtained taken images to generate the second enhanced image, and
a comparing function of comparing the luminance value of the first enhanced image and the luminance value of the second enhanced image at corresponding positions with each other, and adopting the luminance value of a higher luminance to generate the integrated image of the dispensed medicine.

15. A medicine inspection assistance device, comprising:
a plurality of light sources configured to irradiate a surface of a dispensed medicine with light in a plurality of illumination directions different from each other;
an imager configured to image the dispensed medicine; and
a processor configured to:
obtain prescription information;
obtain a master image of a medicine to be dispensed, based on the prescription information;
control the light sources and the imager to obtain a plurality of taken images of the dispensed medicine, with illumination directions of light to the dispensed medicine different from each other;
enhance an engraved mark portion of at least one of the obtained taken images, and generate a first enhanced image of the dispensed medicine;
enhance a printed character portion of at least one of the obtained taken images, and generate a second enhanced image of the dispensed medicine;
integrate the first enhanced image and the second enhanced image with each other to generate an integrated image of the dispensed medicine; and
collate the generated integrated image of the dispensed medicine with the obtained master image, and determine whether the medicine to be dispensed is identical to the dispensed medicine or not,
wherein the processor is further configured to:
reduce a luminance value at the engraved mark portion of the at least one of the obtained taken images to generate the first enhanced image,
reduce a luminance value at the printed character portion of the at ast one of the obtained taken images to generate the second enhanced image, and compare the luminance value of the first enhanced image and the luminance value of the second enhanced image at corresponding positions with each other, and adopt the luminance value of a lower luminance to generate the integrated image of the dispensed medicine.

16. An image processing method, comprising:
a master image obtaining step of obtaining a master image of a medicine to be dispensed, based on prescription information;
a taken image obtaining step of obtaining a plurality of taken images of a dispensed medicine, with emitting directions of light to a surface of the dispensed medicine different from each other;
a first image processing step of enhancing an engraved mark portion of at least one of the obtained taken images, and generating a first enhanced image of the dispensed medicine;
a second image processing step of enhancing a printed character portion of at least one of the obtained taken images, and generating a second enhanced image of the dispensed medicine;
an image integrating step of integrating the first enhanced image and the second enhanced image with each other to generate an integrated image of the dispensed medicine; and
a determining step of collating the generated integrated image of the dispensed medicine with the obtained master image, and determining whether the medicine to be dispensed is identical to the dispensed medicine or not,
wherein the image processing method further comprises:
a first luminance value reducing step of reducing a luminance value at the engraved mark portion of the at least one of the obtained taken images to generate the first enhanced image,
a second luminance value reducing step of reducing a luminance value at the printed character portion of the at least one of the obtained taken images to generate the second enhanced image, and
a comparing step of comparing the luminance value of the first enhanced image and the luminance value of the second enhanced image at corresponding positions with each other, and adopting the luminance value of a lower luminance to generate the integrated image of the dispensed medicine.

17. A non-transitory computer-readable storage medium wherein when an instruction stored in the recording medium is read by a computer, the instruction causes the computer to execute:
a master image obtaining function of obtaining a master image of a medicine to be dispensed, based on prescription information;
a taken image obtaining function of obtaining a plurality of taken images of a dispensed medicine with emitting directions of light to a surface of the dispensed medicine different from each other;
a first image processing function of enhancing an engraved mark portion of at least one of the obtained taken images, and generating a first enhanced image of the dispensed medicine;
a second image processing function of enhancing a printed character portion of at least one of the obtained taken images, and generating a second enhanced image of the dispensed medicine;

an image integrating function of integrating the first enhanced image and the second enhanced image with each other to generate an integrated image of the dispensed medicine; and
a determining function of collating the generated integrated image of the dispensed medicine with the obtained master image, and determining whether the medicine to be dispensed is identical to the dispensed medicine or not,
wherein the instruction causes the computer to further execute:
a first luminance value reducing function of reducing a luminance value at the engraved mark portion of the at least one of the obtained taken images to generate the first enhanced image,
a second luminance value reducing function of reducing a luminance value at the printed character portion of the at least one of the obtained taken images to generate the second enhanced image, and
a comparing function of comparing the luminance value of the first enhanced image and the luminance value of the second enhanced image at corresponding positions with each other, and adopting the luminance value of a lower luminance to generate the integrated image of the dispensed medicine.

18. A medicine inspection assistance device, comprising:
a plurality of light sources configured to irradiate a surface of a dispensed medicine with light in a plurality of illumination directions different from each other;
an imager configured to image the dispensed medicine; and
a processor configured to:
  obtain prescription information;
  obtain a master image of a medicine to be dispensed, based on the prescription information;
  control the light sources and the imager to obtain a plurality of taken images of the dispensed medicine, with illumination directions of light to the dispensed medicine different from each other;
  enhance an engraved mark portion of at least one of the obtained taken images, and generate a first enhanced image of the dispensed medicine;
  enhance a printed character portion of at least one of the obtained taken images, and generate a second enhanced image of the dispensed medicine;
  integrate the first enhanced image and the second enhanced image with each other to generate an integrated image of the dispensed medicine; and
  collate the generated integrated image of the dispensed medicine with the obtained master image, and determine whether the medicine to be dispensed is identical to the dispensed medicine or not,
wherein the processor is further configured to:
calculate a similarity indicating a degree at which the generated integrated image of the dispensed medicine is similar to the obtained master image, and
determine whether the medicine to be dispensed is identical to the dispensed medicine or not, based on the calculated similarity, and
wherein the processor is further configured to:
calculate similarities between a plurality of the generated integrated images of the dispensed medicine and a plurality of the obtained master images, and
determine that the medicine to be dispensed is identical to the dispensed medicine, for a combination of the generated integrated image of the dispensed medicine and the obtained master image with a highest similarity.

19. An image processing method, comprising:
a master image obtaining step of obtaining a master image of a medicine to be dispensed, based on prescription information;
a taken image obtaining step of obtaining a plurality of taken images of a dispensed medicine, with emitting directions of light to a surface of the dispensed medicine different from each other;
a first image processing step of enhancing an engraved mark portion of at least one of the obtained taken images, and generating a first enhanced image of the dispensed medicine;
a second image processing step of enhancing a printed character portion of at least one of the obtained taken images, and generating a second enhanced image of the dispensed medicine;
an image integrating step of integrating the first enhanced image and the second enhanced image with each other to generate an integrated image of the dispensed medicine; and
a first determining step of collating the generated integrated image of the dispensed medicine with the obtained master image, and determining whether the medicine to be dispensed is identical to the dispensed medicine or not,
wherein the image processing method further comprises:
a first calculating step of calculating a similarity indicating a degree at which the generated integrated image of the dispensed medicine is similar to the obtained master image, and
a second determining step of determining whether the medicine to be dispensed is identical to the dispensed medicine or not, based on the calculated similarity, and
wherein the image processing method further comprises:
a second calculating step of calculating similarities between a plurality of the generated integrated images of the dispensed medicine and a plurality of the obtained master images, and
a third determining step of determining that the medicine to be dispensed is identical to the dispensed medicine, for a combination of the generated integrated image of the dispensed medicine and the obtained master image with a highest similarity.

20. A non-transitory computer-readable storage medium wherein when an instruction stored in the recording medium is read by a computer, the instruction causes the computer to execute:
a master image obtaining function of obtaining a master image of a medicine to be dispensed, based on prescription information;
a taken image obtaining function of obtaining a plurality of taken images of a dispensed medicine with emitting directions of light to a surface of the dispensed medicine different from each other;
a first image processing function of enhancing an engraved mark portion of at least one of the obtained taken images, and generating a first enhanced image of the dispensed medicine;
a second image processing function of enhancing a printed character portion of at least one of the obtained taken images, and generating a second enhanced image of the dispensed medicine;
an image integrating function of integrating the first enhanced image and the second enhanced image with each other to generate an integrated image of the dispensed medicine; and
a first determining function of collating the generated integrated image of the dispensed medicine with the obtained master image, and determining whether the medicine to be dispensed is identical to the dispensed medicine or not,
wherein the instruction causes the computer to further execute:
a first calculating function of calculating a similarity indicating a degree at which the generated integrated image of the dispensed medicine is similar to the obtained master image, and
a second determining function of determining whether the medicine to be dispensed is identical to the dispensed medicine or not, based on the calculated similarity, and
wherein the instruction causes the computer to further execute:
a second calculating function of calculating similarities between a plurality of the generated integrated images of the dispensed medicine and a plurality of the obtained master images, and
a third determining function of determining that the medicine to be dispensed is identical to the dispensed medicine, for a combination of the generated integrated image of the dispensed medicine and the obtained master image with a highest similarity.

* * * * *